(12) United States Patent
Turer et al.

(10) Patent No.: US 12,239,776 B2
(45) Date of Patent: *Mar. 4, 2025

(54) SENSING CANNULA SYSTEMS

(71) Applicants: University of Pittsburgh—Of the Commonwealth System of Higher Education, Pittsburgh, PA (US); UPMC, Pittsburgh, PA (US)

(72) Inventors: David Turer, Pittsburgh, PA (US); William W. Clark, Wexford, PA (US); April Lawrence, Pittsburgh, PA (US); Ehsan Qaium, Pittsburgh, PA (US); Joseph P. Rubin, Pittsburgh, PA (US); Cameron Dezfulian, Pittsburgh, PA (US)

(73) Assignees: University of Pittsburgh—Of the Commonwealth System of Higher Education, Pittsburgh, PA (US); UPMC, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/149,394

(22) Filed: Jan. 3, 2023

(65) Prior Publication Data
US 2023/0149620 A1    May 18, 2023

Related U.S. Application Data

(63) Continuation of application No. 17/050,504, filed as application No. PCT/US2019/031815 on May 10, 2019, now Pat. No. 11,547,787.
(Continued)

(51) Int. Cl.
*A61M 1/00* (2006.01)

(52) U.S. Cl.
CPC .............. *A61M 1/743* (2021.05); *A61M 1/73* (2021.05); *A61M 2202/08* (2013.01);
(Continued)

(58) Field of Classification Search
CPC .... A61M 1/743; A61M 1/73; A61M 2202/08; A61M 2205/3584; A61M 2205/581;
(Continued)

(56) References Cited

U.S. PATENT DOCUMENTS

| | | |
|---|---|---|
| 5,063,937 A | 11/1991 | Ezenwa et al. |
| 5,271,413 A | 12/1993 | Dalamagas et al. |

(Continued)

FOREIGN PATENT DOCUMENTS

| | | | | |
|---|---|---|---|---|
| EP | 0646382 A1 | * | 4/1995 | ........ A61M 5/16854 |
| WO | WO-0047254 A1 | * | 8/2000 | .......... A61M 5/1456 |

(Continued)

OTHER PUBLICATIONS

Communication Pursuant to Article 94(3) EPC issued by the European Patent Office in related European Application No. 19799231.6 on Feb. 28, 2023 (6 pp.).
(Continued)

*Primary Examiner* — Ariana Zimbouski
*Assistant Examiner* — Eric Rassavong
(74) *Attorney, Agent, or Firm* — Klarquist Sparkman, LLP

(57) ABSTRACT

Disclosed cannula systems can detect the tissue type within which the cannula tip is located in real time using electrodes adjacent the cannula tip. The sensing cannula system can differentiate when the cannula tip is in adipose tissue or muscle based on electrical impedance. The system can be used in fat grafting and liposuction procedures, for example. An operator can detect if the cannula tip enters muscle by watching for an indicator light or audible alarm that is
(Continued)

automatically activated by the device based on a change in sensed impedance. The device may also stop the flow of fat through a pump halting injection into the sub-muscular space.

22 Claims, 23 Drawing Sheets

Related U.S. Application Data

(60) Provisional application No. 62/736,813, filed on Sep. 26, 2018, provisional application No. 62/697,596, filed on Jul. 13, 2018, provisional application No. 62/669,781, filed on May 10, 2018.

(52) U.S. Cl.
CPC ............... *A61M 2205/3584* (2013.01); *A61M 2205/581* (2013.01); *A61M 2205/584* (2013.01); *A61M 2205/587* (2013.01); *A61M 2230/65* (2013.01)

(58) Field of Classification Search
CPC ...... A61M 2205/584; A61M 2205/587; A61M 2230/65; A61B 5/4887; A61B 5/6848; A61B 5/0538; A61B 5/4836; A61B 2505/05; A61B 5/0537; A61B 5/6865; A61B 2230/65
See application file for complete search history.

(56) References Cited

U.S. PATENT DOCUMENTS

| | | | |
|---|---|---|---|
| 5,335,668 | A | 8/1994 | Nardella |
| 5,935,066 | A | 8/1999 | Harris |
| 6,024,704 | A | 2/2000 | Meador et al. |
| 6,337,994 | B1 | 6/2002 | Stoianovici et al. |
| 6,847,841 | B1 | 1/2005 | El Hatw |
| 7,845,537 | B2 | 12/2010 | Shelton, IV et al. |
| 8,323,279 | B2 | 12/2012 | Dahla et al. |
| 8,489,172 | B2 | 7/2013 | Gelbart et al. |
| 9,597,482 | B2 | 3/2017 | Hann |
| 10,022,059 | B2 | 7/2018 | Fischell et al. |
| 10,154,792 | B2 | 12/2018 | Sakai et al. |
| 10,271,866 | B2 | 4/2019 | Clark, III et al. |
| 10,434,278 | B2 | 10/2019 | Dunbar et al. |
| 11,517,722 | B2 | 12/2022 | Ma et al. |
| 11,547,787 | B2 | 1/2023 | Turer et al. |
| 2001/0049510 | A1 | 12/2001 | Burr et al. |
| 2005/0267455 | A1 | 12/2005 | Eggers et al. |
| 2007/0225686 | A1 | 9/2007 | Shippert |
| 2008/0306391 | A1 | 12/2008 | Hular et al. |
| 2009/0118610 | A1 | 5/2009 | Karmarkar et al. |
| 2009/0192441 | A1 | 7/2009 | Gelbert et al. |
| 2010/0286507 | A1 | 11/2010 | Paassilta et al. |
| 2012/0108950 | A1 | 5/2012 | He et al. |
| 2013/0226114 | A1* | 8/2013 | Massi ................... A61M 1/743 604/327 |
| 2014/0081244 | A1 | 3/2014 | Voeller et al. |
| 2015/0025521 | A1 | 1/2015 | Friedrichs et al. |
| 2015/0173636 | A1 | 6/2015 | Mokelke et al. |
| 2015/0216442 | A1 | 8/2015 | Lavy et al. |
| 2015/0314105 | A1 | 11/2015 | Gasparyan et al. |
| 2015/0359991 | A1 | 12/2015 | Dunbar et al. |
| 2016/0029920 | A1 | 2/2016 | Kronstrom et al. |
| 2016/0096010 | A1* | 4/2016 | Klein ................. A61M 5/31501 604/514 |
| 2016/0135842 | A1 | 5/2016 | Kassab |
| 2016/0158502 | A1 | 6/2016 | Kume et al. |
| 2017/0333623 | A1* | 11/2017 | Kamen ............... A61M 5/1408 |
| 2017/0354379 | A1 | 12/2017 | Goyal et al. |
| 2018/0317801 | A1 | 11/2018 | Lee et al. |
| 2020/0206471 | A1 | 7/2020 | Dezfulian et al. |

FOREIGN PATENT DOCUMENTS

| | | | |
|---|---|---|---|
| WO | 2009019707 A1 | 2/2009 | |
| WO | WO-2012092948 A1 * | 7/2012 | .......... A61M 1/0025 |
| WO | 2016034910 | 3/2016 | |
| WO | 2016040394 | 3/2016 | |

OTHER PUBLICATIONS

Extended Search Report for related EP Application No. 19799231.6, 8 pages, mailed Jan. 27, 2022.
Injeq IQ-Needle™ Precision. Care. Confidence., https://injeq.com/, 5 pages, downloaded Mar. 18, 2019.
International Search Report and Written Opinion for related International Application No. PCT/US2018/040952, 9 pages, mailed Oct. 28, 2018.
International Search Report and Written Opinion for related International Application No. PCT/US2019/031815, 8 pages, mailed Sep. 22, 2019.
Sharp et al., "Tissue type determination by impedance measurement: A bipolar and monopolar comparison," Saud J. Anaesth 11:15-20, 2017.
Trebbels et al., "Real-Time Cannula Navigation in Biological Tissue with high temporal and spatial resolution based on Impedance Spectroscopy," 32nd Annual International Conference of the IEEE EMBS, Buenos Aires, Argentina, 4 pages (Aug. 31-Sep. 4, 2010).
International Search Report and Written Opinion for International Application No. PCT/US2020/024240, 15 pages, mailed Jun. 25, 2020.

* cited by examiner

SENSING CANNULA SYSTEMS

CROSS-REFERENCE TO RELATED APPLICATIONS

This application is a continuation of U.S. patent application Ser. No. 17/050,504, filed Oct. 26, 2020, which is the U.S. National Stage of International Application No. PCT/US2019/031815, filed May 10, 2019, which claims the benefit of U.S. Provisional Patent Application Nos. 62/669,781 filed May 10, 2018; 62/697,596 filed Jul. 13, 2018; and 62/736,813 filed on Sep. 26, 2018; which are all incorporated by reference herein in their entireties. International Patent Application No. PCT/US2018/040952 filed Jul. 5, 2018 also describes technology related to the instant disclosure and is also incorporated by reference herein in its entirety.

STATEMENT OF GOVERNMENT SUPPORT

This invention was made with government support under grant #1449702 awarded by the National Science Foundation. The government has certain rights in the invention.

FIELD

This application relates to cannula systems for transporting fluids in and out of patients, and sensing systems for cannula-based procedures.

BACKGROUND

The process of transplanting fat from one part of the body to another is known as fat grafting. This is a common technique used in a variety of plastic and reconstructive surgery procedures. Commonly, fat is lipo-suctioned and then re-injected through thin metal cannulas. For example, the buttock auto-augmentation (commonly known as the "Brazilian butt lift"), has become a popular cosmetic procedure. In this procedure, fat is lipo-suctioned from the abdomen and thighs, and reinjected into the buttocks. Unfortunately, this procedure has been plagued by a number of patient deaths due to fatal fat embolism. It is believed that this complication is caused by injury to the vessels that lie under and within the gluteal muscles, which then allows the injected fat to travel into the veins and back to the lung causing fat embolism. Autopsy has demonstrated intramuscular injection of fat in all of the patients with fatal complications. The mortality rate of this procedure is approaching 1 in 3000 patients, higher than almost any other procedure in elective plastic surgery.

At the present time, there are no devices or technologies being employed to improve the safety of liposuction or fat grafting procedures. There are a variety of techniques that all include careful positioning of the patient and cannula to avoid inadvertent injury to deeper structures, but these all rely on the experience and skill of the individual surgeon. Real time ultrasound imaging can be employed, but is expensive, cumbersome, and can require special training by the surgeon.

SUMMARY

Cannula systems disclosed herein can detect the tissue type within which the cannula tip is located in real time. The "smart" sensing cannula can differentiate when the cannula tip is in adipose tissue or muscle based on electrical impedance. Since the anatomic danger zone lies beneath the muscle in the medial aspect of the buttocks, an operator can detect when the cannula enters muscle watching for an indicator light or audible alarm that is automatically activated by the device. The device may also be able to stop the flow of fat through a pump halting injection into the sub-muscular space.

In one embodiment disclosed herein, the device is based on a standard stainless-steel liposuction cannula. A removable sheath is placed over the cannula which mechanically and electrically couples with the cannula. The cannula itself serves as one electrode and another electrode is present on the sheath. Except for the exposed distal electrodes, the rest of the sheath is electrically insulated.

The sensing circuitry can operate by measuring the potential difference between the electrodes, which can then be fed through operational amplifiers, which serve as an oscillator to create a square wave with an output frequency proportional to the measured potential. As the impedance of the tissue at the cannula tip changes, the frequency of the output signal will change proportionally as well. This can then be processed by a microcontroller that measures the frequency of the signal and then activates lights, sounds, or other indicator to indicate the kind of tissue sensed by the device. This can be done with wired or wireless transmission. In one example at uses LED indicators, three colors (green, red and blue) correspond to the frequency ranges appropriate for fat, muscle and air (open circuit) respectively. An audible warning also sounds when the device senses it is in muscle. In some embodiments, a variable sound warning can correspond the varying impendence level (e.g., variation in sound frequency and/or variation in sound amplitude). In some embodiments, a change in impedance detected by the cannula can result in a signal that shuts off an infusion pump, closes a valve, impedes the action of a syringe used for injection, or otherwise prevents the further flow of fat tissue through the cannula.

The circuitry and battery for the sensors can be mounted on the cannula, built into the design of the cannula, or be separate from the cannula.

A bench validation study was performed using fresh porcine tissue with thick enough adipose and muscle layers so that the tip of the cannula can be placed within either tissue type and not contact any elements of the other tissue type (fat versus muscle). One hundred observations were made with the tissue type selected at random and the operator blinded to the results of the tissue type detected by the system. Once the cannula was within the selected tissue, the observer recorded the reading from the sensor. The system was able to differentiate between muscle and fat with 100% accuracy.

Subsequently, the sensing cannula was then taken to a cadaver laboratory and inserted into the tissue planes in the gluteal region through a port site, simulating the gluteal fat grafting procedure. Ultrasound was used to detect when the tip of the cannula was in subcutaneous adipose tissue versus muscle. Readings from the device were correlated with the ultrasound findings to confirm the ability to differentiate muscle from adipose tissue.

This exemplary "smart" sensing cannula is able to detect when the tip of the cannula is in adipose tissue or muscle based on electrical impedance and will alert the operator as to the type of tissue in which the cannula tip currently resides. The cannula can comprise stainless steel or any other suitable materials. Existing cannulas can also be retrofit with a removable sheath that houses the sensing electrodes to employ the disclosed technology.

Without the disclosed technology, an operator may need to rely on real-time ultrasound to detect the position of the cannula tip. However, the operator needs a significant amount of skill in reading ultrasound images to determine the position of the cannula and to be able to track the cannula tip with the ultrasound probe during the procedure. This may also add significant time and cost to the procedure. An advantage of the sensing cannula is that no additional skill may be needed on the part of the operator. Moreover, this disclosed device can be used with a lower entry cost and made more widely available, as opposed to ultrasound, which may require more significant equipment costs and training.

The technology disclosed herein has the advantages of high accuracy and resolution, low cost of production, and no special training may be required by the surgeon to use the device. Additionally, this technology can be adapted to virtually any cannula configuration.

The foregoing and other objects, features, and advantages of the disclosed technology will become more apparent from the following detailed description, which proceeds with reference to the accompanying figures.

DETAILED DESCRIPTION

The devices and systems disclosed herein are intended to improve the safety of both liposuction and fat grafting procedures by alerting the operator when the cannula passes out of the subcutaneous fat tissue plane and into deeper layers where vital structures could be injured. Furthermore, a function of the device enables the flow of fat to be immediately stopped when a tissue layer is detected that is problematic.

In 2016, there were over 400,000 liposuction procedures and over 18,000 buttock auto-augmentation procedures in the US alone. This device can potentially be used in any or all of these procedures.

An example of one variation of the device, shown below, combines a metal luer-lock cannula with two electrodes at the tip in order to measure tissue impedance. Different kinds of tissues have different electrical impedances. For example, the impedance of fat is significantly higher than muscle or blood. Using this property, it is possible to use tissue impedance to determining the type of tissue in which the device resides. The tip of the cannula itself can serve as one of the electrodes, but this is not mandatory and it may be desirable to have electrodes electrically separate from the cannula itself. The electrodes are connected to wires at the base of the cannula and then to a proprietary impedance sensing system, which has been previously described. An audible alert or visual indicator (e.g. red light or blinking strobe) can be enabled to notify the surgeon when certain impedance thresholds are reached, and can simultaneously trigger a valve or other mechanism to stop the flow of fat.

Figure 1:
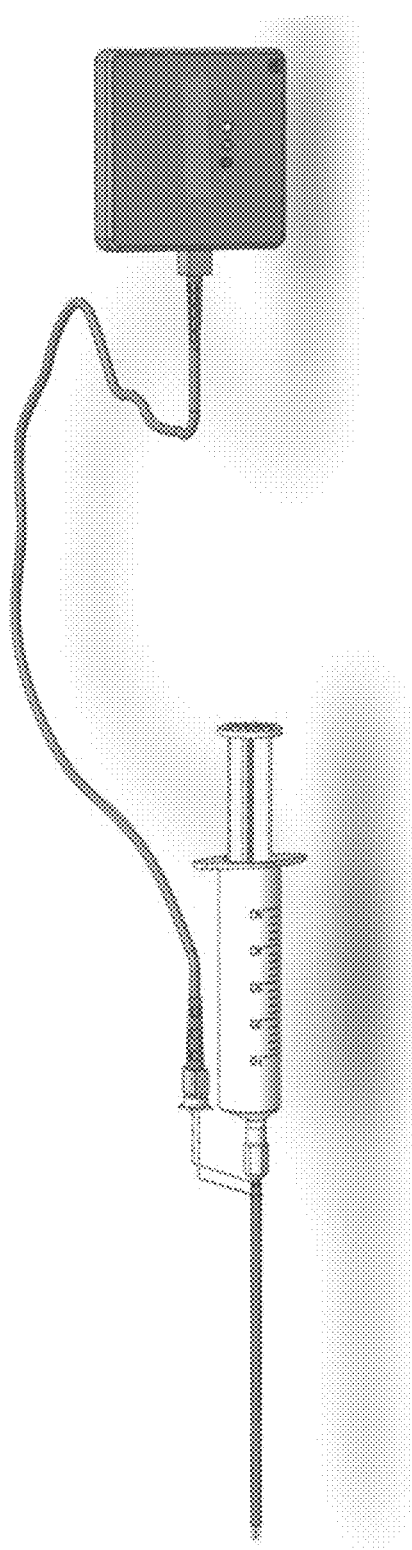
FIG. 1 shows an exemplary cannula system with electrodes coupled to a detection unit.

Shown in FIG. 1 is a schematic of the technology that includes a detection unit, a cannula that is coupled with a syringe for injection or suction of fat and that is instrumented with electrodes for detection of tissue type, and wires providing the electrical connection to the detection unit. In some embodiments, the detection unit can be coupled to and decoupled from the cannula via a quick-connect type of connector, such as a BNC connector. An additional feature of the system is an actuation system that can automatically stop the flow of fat. Several design combinations are presented in this application for the system.

The disclosed technology, as described below, measures the resistance of materials that the cannula contacts as it is inserted. The resistance values can be used to indicate progress of the cannula through tissue, and can indicate when, for example, muscle has been contacted. This information can be used through various algorithms and hardware to alert the user, and/or automatically stop the flow of suctioned or injected material.

Tissue or fluid resistance constitutes a resistor that can be measured by different techniques. An exemplary embodiment of the detection circuit (described below) can include an oscillator whose frequency of oscillation depends on the quantities of connected resistor and capacitor components. In the present embodiment, the tissue or fluid resistance between the two electrodes on the cannula (one of which can be the cannula body itself) make up a key resistor component in the circuit. Different resistances (e.g. fatty tissue under the skin vs. blood or muscle tissue) cause the frequency of oscillation to change. By measuring this frequency, the type of tissue in contact with the cannula, and thus the location of the cannula can be determined.

Figure 2:
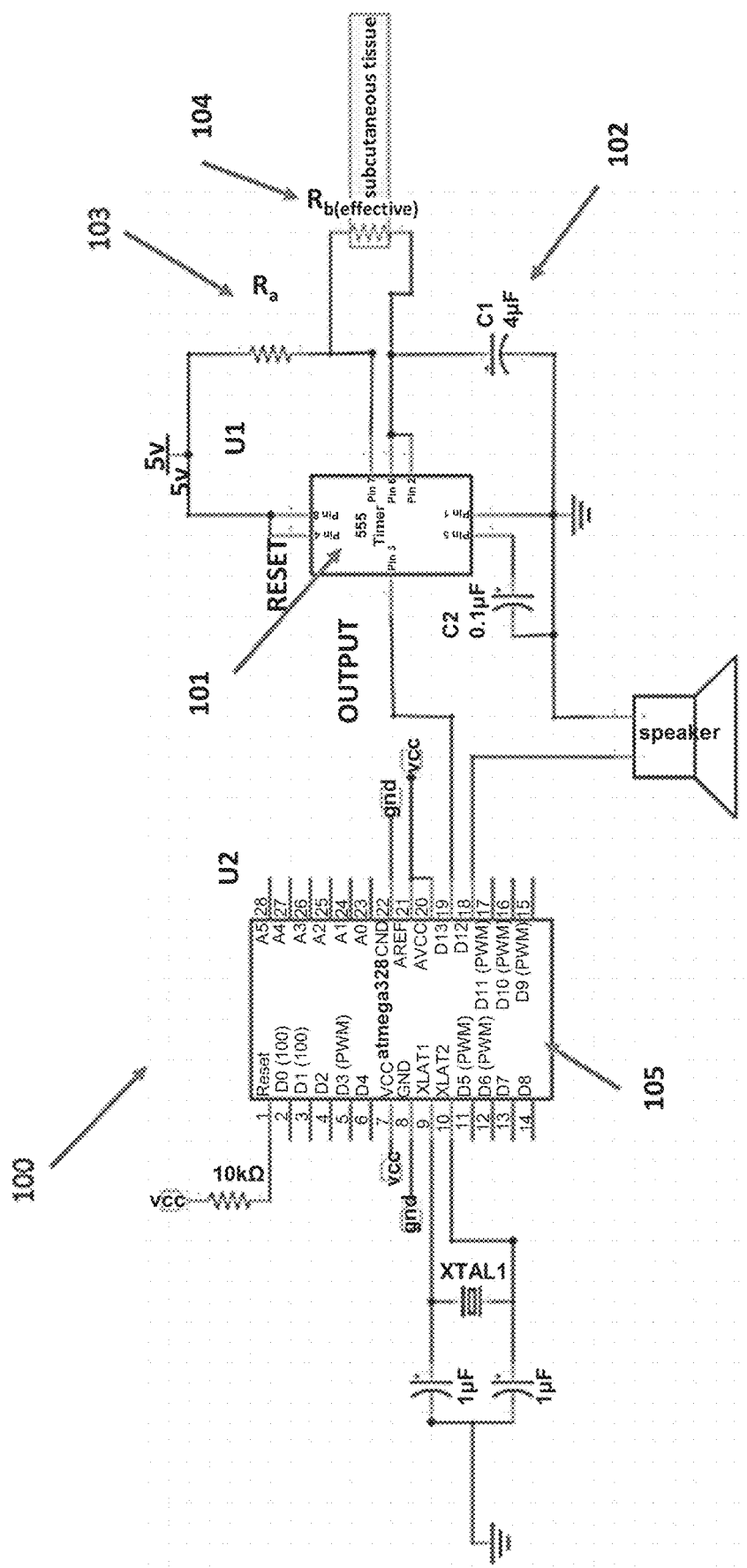
FIG. 2 is a circuit diagram of a 555 timer circuit in astable mode where $R_b$ is made up of the tissue resistance between the two electrodes ($R_{effective}$). The signal from the timer circuit can be sent to a microcontroller, which can measure the frequency and can alert the user to a change, such as through an audible tone.

FIG. 2 displays an example of a circuit diagram (as described above) for the detection unit (100), although other types of timing circuits may be used. The circuit can comprise a timer chip (101) (e.g., a 555 chip), a capacitor of pre-determined value (102) (e.g., a 4.7 µF capacitor), and resistors $R_a$ (103) (pre-determined, e.g., 675Ω), $R_{effective}$ (104) the unknown resistance of the tissue and a microcontroller. As shown in FIG. 2, the two electrodes can be connected to the circuit through extension wires and the tissue/fluid resistance becomes the effective resistance $R_{effective}$ Although only subcutaneous tissue is shown in FIG. 2, the cannula can encounter other materials such as blood and muscle during use. The 555 chip is a timer chip that can be used to generate time delays or oscillation. It can have two modes of operation, mono stable (time delay), and astable (oscillator). A preferred use in this system is in astable mode.

Figure 3:
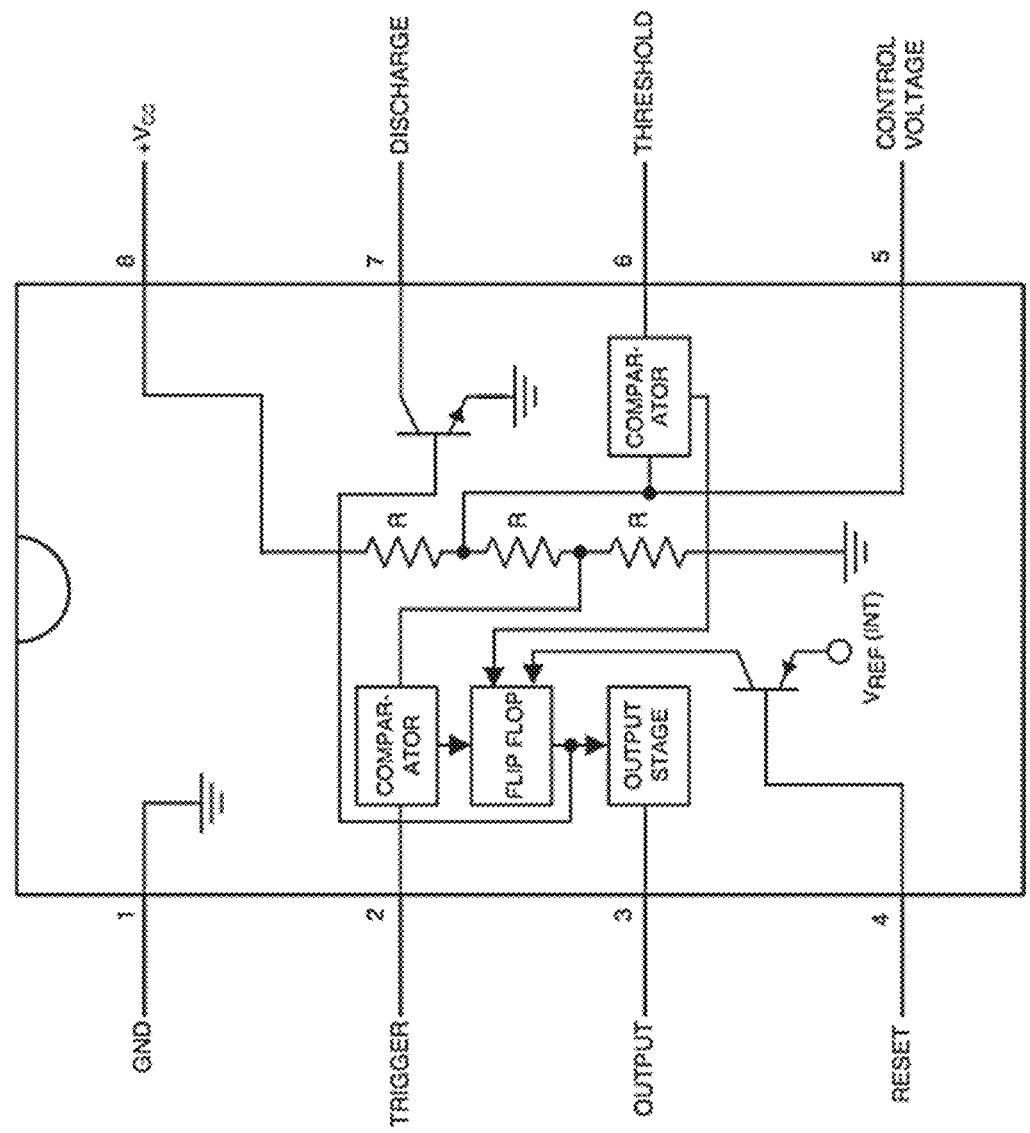
FIG. 3 is an internal circuit diagram of a 555 timer.

An exemplary operation of the 555 timer chip (as well as other example timer circuits) is described here to clarify how it can be used to measure tissue/fluid resistance in the disclosed systems. FIG. 3 displays the internal circuitry of the 555 timer. The internal circuit of the timer can comprise three 5 KΩ resistors, two comparators that compare two input voltages (labeled V+ and V−), a flip flop, an output stage, and two transistors. In astable mode, a voltage ($V_{CC}$) is provided across the resistors $R_a$ and $R_{effective}$ (the unknown tissue/fluid resistance) (104), which in turn starts charging the capacitor (102). Once the capacitor reaches some percentage of the supply voltage (for example ⅔) it discharges through the transistor in pin 7 and $R_{effective}$ Once discharged the capacitor starts re-charging through resistors $R_a$ and $R_{effective}$ While the capacitor is charging, the first comparator connected to pin 2 compares the input voltage from the trigger pin to a reference voltage that is a percentage of We (for example, ⅓). At the same time, the second comparator compares the input voltage from the threshold pin (pin 6) to a reference voltage (for example, ⅔ $V_{CC}$) from the voltage divider. When the input voltage (V+) is higher than the reference voltage (V−) the comparator outputs a logic 1 or if V− is higher than V+ then the comparator outputs a logic 0.

The outputs from the two comparators are connected to the flip flop which produces either a logic 1 or a logic 0 signal based on the state of the inputs. Next, the output signal from the flip flop travels to the output stage. When the output stage receives a logic input of 0 from the flip flop it outputs a digital high voltage at that time. Subsequently when a logic input of 1 is received by the output stage, pin 3 is connected to ground, and the transistor in pin 7 is opened allowing the capacitor to discharge. This process continuously repeats while the timer is operating in astable mode producing a clocking signal (oscillating binary output in the form of a rectangular wave) outputted via pin 3 whose signal is sent to a microcontroller (e.g. ATmega328p). The frequency of the rectangular wave is dependent on the relative values of the resistors (103 and 104) and the capacitor (102) and in this scenario is used specifically to determine the resistance or change in resistance of the unknown tissue (104). Other component values can be determined using related methods. While use of the 555 timer chips is one method for relating resistance to oscillation frequency, it is not the only method that can be used. Any suitable method that uses a time-constant of a resistor-capacitor or resistor-inductor circuit to create a dynamic response or an oscillating signal can be used as well to relate the time characteristics of the signal to the unknown resistance, capacitance, and/or inductance.

The microcontroller (105) is responsible for measuring the frequency of the signal produced by the timer chip (pin 3). There are several options for conveying a detected change to the end user. One option is based on the absolute value of the measured frequency (or resistance) and the other is based on a change in measured frequency (or resistance).

When using the absolute value method, a threshold can be set (e.g. frequency<100 Hz for fatty tissue) the end user can be alerted to contact with muscle or blood through output interfaces (FIG. 4) if the measured frequency value is greater than the specified cutoff. (Note that in the circuit (100) describe here, signal oscillation frequency is inversely dependent on resistance (104), so as resistance decreases, for example when the electrodes pass from fatty tissue to blood, the signal frequency increases. Other circuits can be configured so as to produce a proportional relationship between frequency and resistance. In addition, methods in which the duty cycle is measured as related to an unknown resistance, capacitance, or inductance are also viable approaches.) Setting an absolute threshold is ideal when a large separation exists between the two quantities being compared. Conversely, the absolute value method presents a problem if the two quantities being compared (e.g. blood vs. muscle) do not have a significant separation between them.

An alternative is to look for a change in baseline (or nominal or initial) frequency due to a change in resistance. This can be accomplished by setting the initial value when the cannula (electrodes) first enters the tissue, for example when the measured resistance changes from air (open circuit) to skin and/or fatty tissue. The frequency observed when the electrodes are in fatty tissue can be set as the baseline and for example can be stored in memory. As the cannula is advanced the user can be alerted to the change when the initial recorded frequency value rises by a certain amount (e.g. 25% increase). The algorithm within the microcontroller can monitor absolute value compared to a threshold, percentage change compared to a baseline, a combination of these changes, or other methods are possible.

The relationship between the rectangular wave frequency and the unknown resistance value ($R_{effective}$) of the tissue/fluid is described by Equation 1. Solving Equation 1 for $R_{effective}$ as shown by Equation 2 provides an expression for the unknown resistance as a function of the measured frequency. It is not necessary to convert the measured frequency values to resistance. This is possible because subcutaneous tissue and blood exhibit distinctive frequencies when their resistance is measured in this way that allow for differentiation between the two quantities and detection of vessel entry. The nominal output frequency of the system is controlled by selecting the values of the resistor $R_a$ and capacitor C. Choosing a large capacitor value increases the cycle time of the system, which in turn reduces output frequency; and increasing $R_a$ increases the high time (the amount of time spent at the top of the rectangular wave) while leaving the low time (the amount of time spent at the bottom of the rectangular wave) unaffected. The respective values of C (4.7 µF) and $R_a$ (675Ω) are shown as examples that produce reasonable separation between subcutaneous tissue and blood, but many other values are feasible.

$$f = \frac{1}{T} = \frac{1.44}{(R_a + 2R_{effective})C} \quad (1)$$

$$R_{effective} = \frac{1}{2}\left(\frac{144}{fC} - R_a\right) \quad (2)$$

Figure 4:
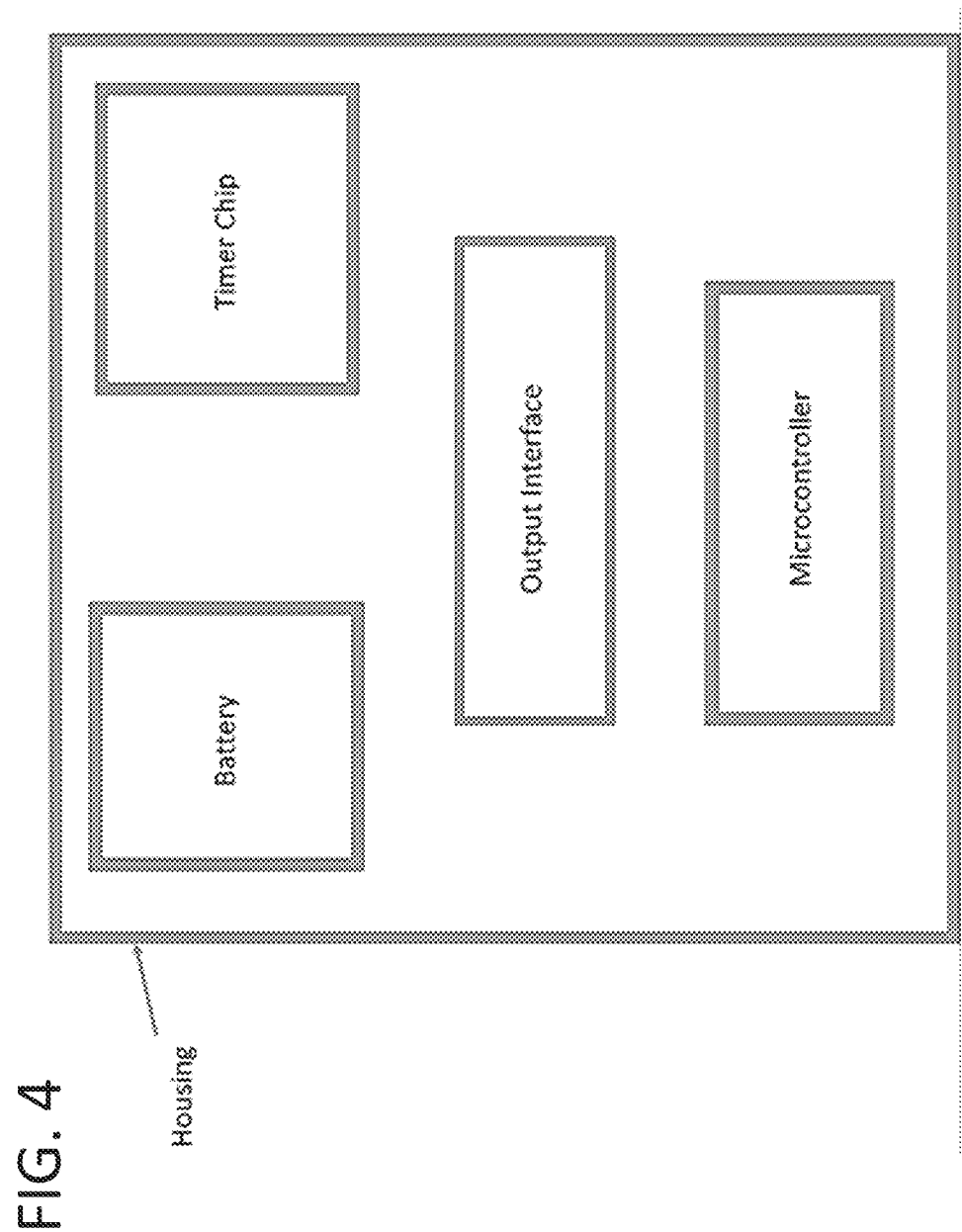
FIG. 4 is a schematic of components of a detection unit, including a battery, timer circuit, microcontroller, and output interfaces.

Shown in FIG. 4 is a schematic of components of the detection unit. Exemplary embodiments comprise a battery to power the device, timer circuit (or alternative oscillatory component or circuit), microcontroller (frequency measurement and interface control), and output interface(s) such as speaker, LED or other light output, vibratory or other tactile interface, and/or LCD or other alpha numeric or graphical display, and power electronics to power actuator(s) to control flow through the cannula. The components of the detection unit, some of which may be mounted on a printed circuit board, are packaged within a small housing (e.g. 2 in×2 in) which will allow the overall system to be portable and optionally mounted onto the cannula and syringe system.

In addition to the components shown in FIG. 4, it is possible to add a radio component to the detection unit (for example a Bluetooth or WiFi or other radio) that enables the system to communicate wirelessly to a mobile device (e.g. a cell phone) or a network or a computer such that the information (measured frequencies and/or resistance values) can be transferred to such devices, computers, and/or networks. Software applications can execute on the devices (e.g. an app on a mobile phone or computer or software on a server) that can receive, analyze, and/or store the data (for example in a database in a server). In such cases the human interface (e.g. lights, sounds, vibrations, etc.) can be presented on the mobile device or on some other device connected to a computer in addition to or in place of the output interface(s) of the detection unit. A software application on a mobile device or computer can be configured to enable the hardware (electrode system, detection unit, or a combination) to operate the same or differently for medical procedures other than liposuction or fat injection. In such a scenario, for example in which a cell phone is wirelessly connected to the detection unit, the user can select in the app what procedure is to be executed, and information can be transferred from the phone to the detection unit to establish operating methods in the microcontroller. For example, one or more parameters can be passed to the microcontroller to indicate that fat injection is the procedure of interest, so associated frequency or resistance values can be measured or passed back to the mobile device or computer or network to be analyzed, stored (for example in a database on the network or in the mobile device or computer) or to be used to alert the user. The information transferred from the detection unit can be measurement of frequency or resistance at specific times (e.g. periodically) or based on events (e.g. changes in frequency or alerts that a frequency threshold has been crossed), or it can be alerts that certain events have occurred. Alternatively, data from the detection unit can be streamed in real time to the mobile device or computer or network so that it may be analyzed in real time to be used immediately by the user or the system or be stored for future use.

An alternative to using the detection unit as depicted in FIG. 1 is to place the circuit into the cannula system itself. In this case it can be referred to as a detection circuit instead of a detection unit. The detection circuit can be miniaturized (including the components of FIG. 4) onto a printed circuit board or as a system-on-a-chip such that it can be included as an integral part of the cannula system, thereby eliminating the need for a separate detection unit shown in FIG. 1. In such case there may be a radio included for wireless communication with a detection unit, or a mobile device as described above, or the circuit can be connected directly to the mobile device or computer through wires. When wired directly, certain functions can be carried out by the mobile device or computer thereby allowing elimination of that related component from the detection circuit, for example eliminating the microcontroller in the detection circuit (and carrying out the analysis and control on the mobile device), or eliminating the battery (whereby the detection circuit is powered from the mobile device through wires), or eliminating the timer circuit (in which case timing or oscillator generator or similar function is executed on the mobile device or computer), or eliminating the output interface (and using the user interfaces on the mobile device to relay information and alerts to the user), or eliminating combinations of these components.

An alternative to using a timer circuit or another oscillating circuit for measuring the unknown tissue/fluid resistance is to utilize a Wheatstone bridge and alternating current (AC). Unlike DC bridges, where the resistance can be directly measured, AC bridges measure the impedance. Equation 3 displays a general expression for impedance, where R is the real component and jX is the imaginary component.

$$Z = R + jX \quad (3)$$

An AC bridge is used instead of DC in order to negate the effect of polarization. Applying a direct current to a liquid solution causes an accumulation of ions near the surface of the electrodes which leads to the polarization of the measurement electrodes and thus erroneous results. Applying alternating current forces the ions to continuously migrate from one electrode to the other thus effectively negating the effect of polarization.

Figure 5:
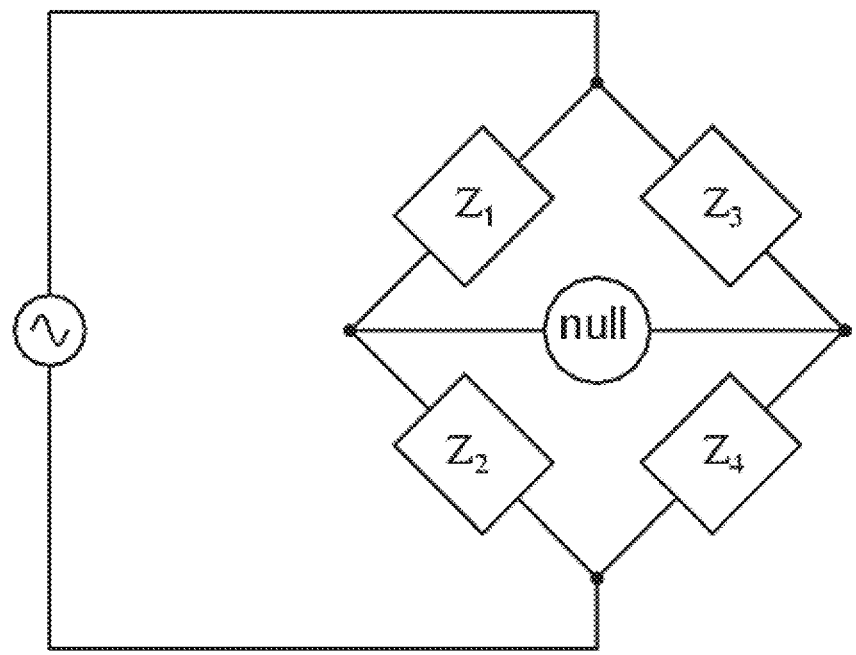
FIG. 5 is a schematic of a balanced AC Wheatstone bridge, where $Z_1$, $Z_2$, $Z_3$, $Z_4$ are the impedances, and "null" indicates an output bridge voltage in the balance condition.

Shown in FIG. 5 is a schematic of a balanced AC Wheatstone bridge, where given an arbitrary AC voltage $Z_1$, $Z_2$, $Z_3$, $Z_4$ are the resulting impedances, and "null" indicates an output bridge voltage in the balance condition. The operation of an AC Wheatstone bridge (as well as other example bridges) is well known and is described here to clarify how it is used to measure tissue/fluid resistance in the disclosed system. The bridge circuit works as a voltage divider when connected to a power source. A specific input voltage will result in a corresponding output voltage. A balanced condition occurs when the voltage difference and current flow between the two legs is zero. A balanced condition results in the output bridge voltage being negligible or "null" (FIG. 5). This allows for the determination of the balance condition (Equation 4). The relationship states that in order for the bridge to balance, the ratio of the impedances of any two adjacent arms usually must equal the ratio of the impedances of the remaining two arms.

$$\frac{Z_1}{Z_2} = \frac{Z_3}{Z_4} \qquad (4)$$

Figure 6:
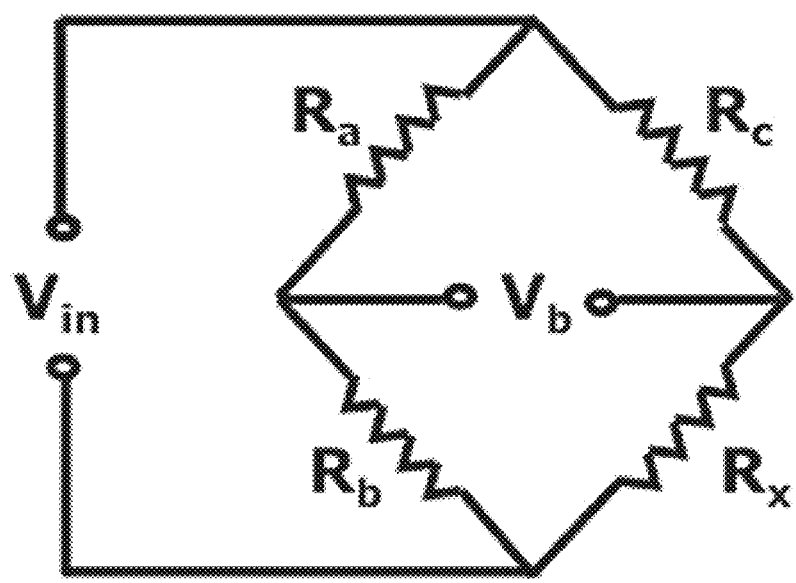
FIG. 6 is a schematic of a Wheatstone bridge, with impedances shown as pure resistors, in an arbitrary unbalanced condition, where $V_b$ is the unbalanced voltage, $V_{in}$ is the input voltage $R_a$, $R_b$, and $R_c$ are known resistance components, and $R_x$ is the unknown component.

FIG. 6 shows the schematic of a Wheatstone bridge, with impedances shown as pure resistors, in an arbitrary unbalanced condition. For a given input the output of the bridge will reflect the extent of the unbalance as, $V_b$ is the unbalanced voltage, $V_{in}$ is the input voltage $R_a$, $R_b$, and $R_c$ are known resistance components, and $R_x$ is the unknown component (FIG. 6). In the present application, the imaginary component of the bridge is neglected and only the real portion considered since the fluid/tissue resistance is the dominant effect. Other bridge configurations are possible, for example using "dummy" resistors to account for unwanted noise and errors.

Applying the voltage divider relationship (Equation 5) an expression is obtained which allows for the determination of the unbalanced voltage for a given input (Equation 6). The unbalanced voltage in the bridge circuit is measured by a microcontroller (e.g. ATmega328p) which measures the unbalanced voltage and alerts the user to vessel entry through an audible tone or other interfaces (FIG. 7).

$$v_b = \frac{R_b}{R_a + R_b} v_{in} \qquad (5)$$

$$v_b = v_{in}\left(\frac{R_x}{R_x + R_c} - \frac{R_b}{R_b + R_a}\right) \qquad (6)$$

Figure 7:
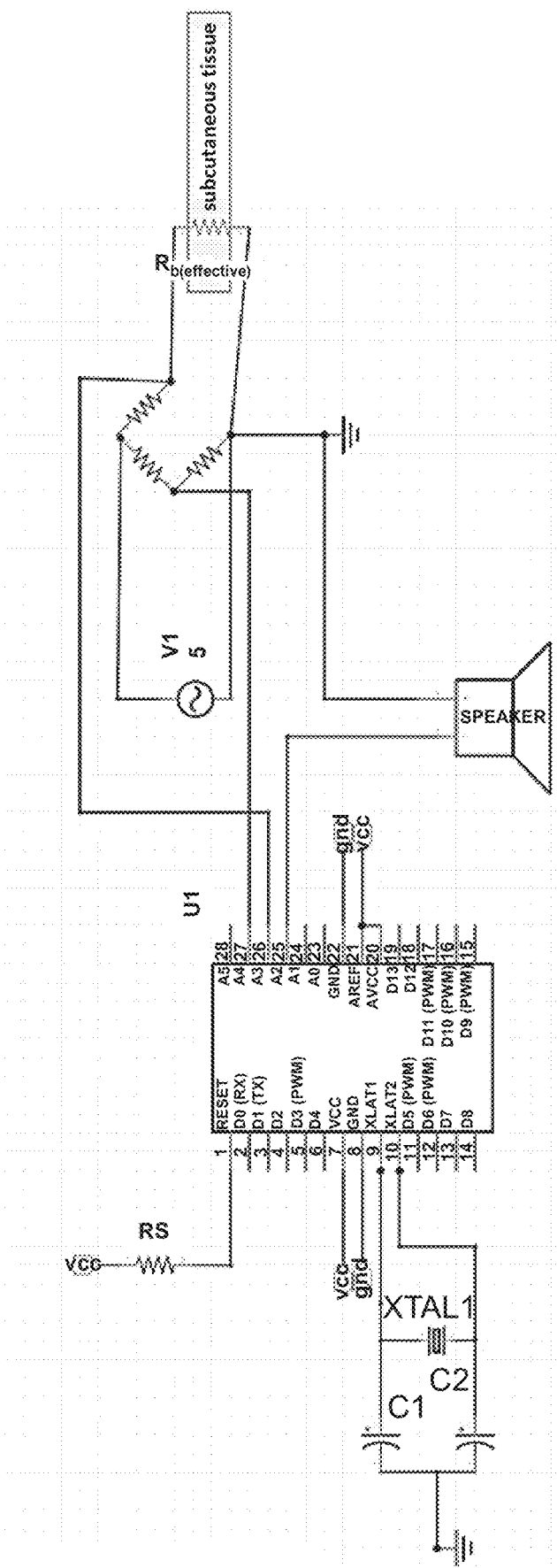
FIG. 7 is a circuit diagram of the wheatstone bridge where $R_x$ is made up of the tissue resistance between the electrodes ($R_{effective}$). The value of the unbalanced voltage is sent to a microcontroller, which alerts the operator to a change.

In the present application, the tissue/fluid being measured will take the place of the resistance value $R_x$, as depicted in FIG. 7. Although only subcutaneous tissue is shown in FIG. 7, it should be noted that the cannula may encounter other materials such as blood and muscle during use. In the current arrangement, the unknown tissue/fluid resistance can be determined by using Equation 7 which in turn allows for the differentiation between subcutaneous tissue and blood. It is not necessary to convert the measured unbalanced bridge voltage values to their corresponding resistance values. This is possible because subcutaneous tissue and blood have distinct unbalanced voltages that can be measured using a microcontroller as mentioned above.

$$R_x = \frac{\left(R_b R_c + \frac{V_b}{V_{in}}(R_a + R_b)\right)}{\left(R_a \frac{V_b}{V_{in}}(R_a + R_b)\right)} \qquad (7)$$

Figure 8:
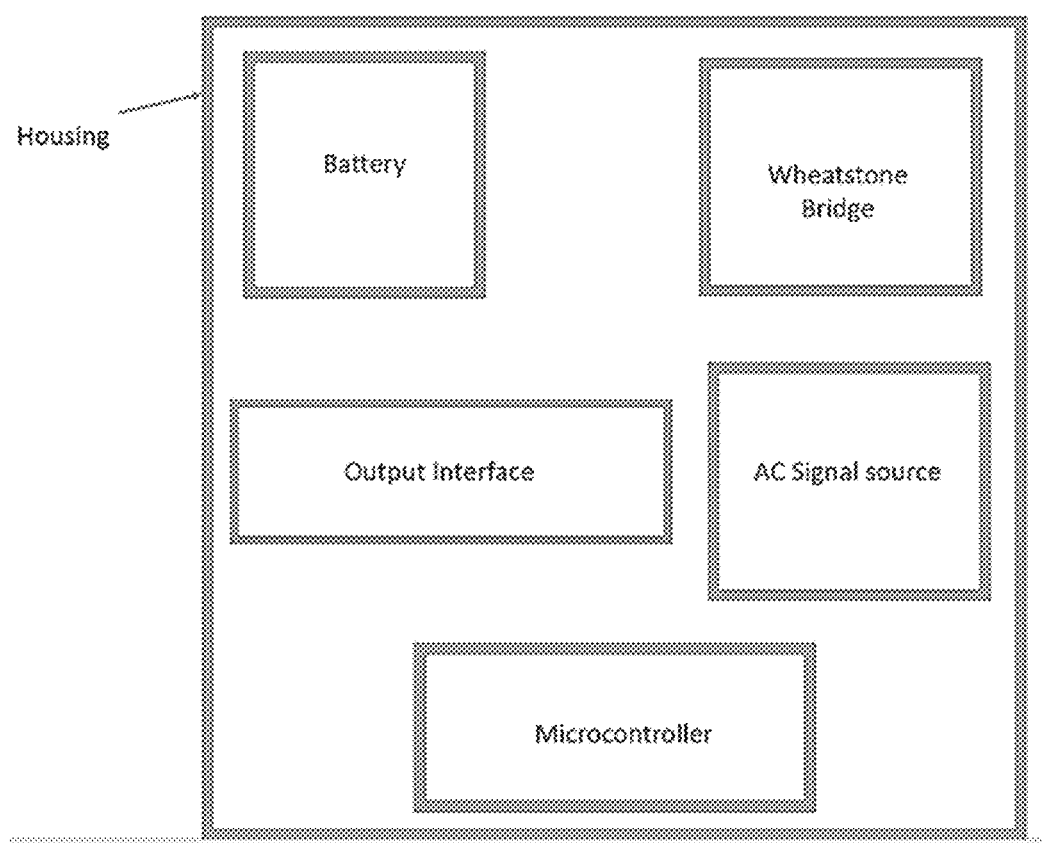
FIG. 8 is a schematic of components of the detection unit, including a battery, an AC signal source, Wheatstone bridge circuit, microcontroller, and output interfaces.

Shown in FIG. 8 is a schematic of components of the alternate detection unit. Exemplary embodiments can comprise a DC battery source to power the device, Wheatstone bridge circuit, an AC signal source for the Wheatstone bridge, a microcontroller (unbalanced voltage measurement and interface control), power electronics for actuator(s), and output interface(s) such as such as speaker, LED or other light output, vibratory or other tactile interface, and/or LCD or other alpha numeric or graphical display which will notify the user of vein entry. The components of the detection unit, some of which may be mounted on a printed circuit board, are packaged within a small housing (e.g., 2 in×2 in) which will allow the overall system to be portable.

Exemplary Sensing Cannula Systems

An example of one variation of the device combines a metal Luer-lock cannula with two electrodes in order to measure tissue impedance. Different kinds of tissues have different electrical impedances. For example, the impedance of fat is significantly higher than muscle or blood. Using this property, it is possible to use tissue impedance to determining the type of tissue in which the device resides.

Figure 9:
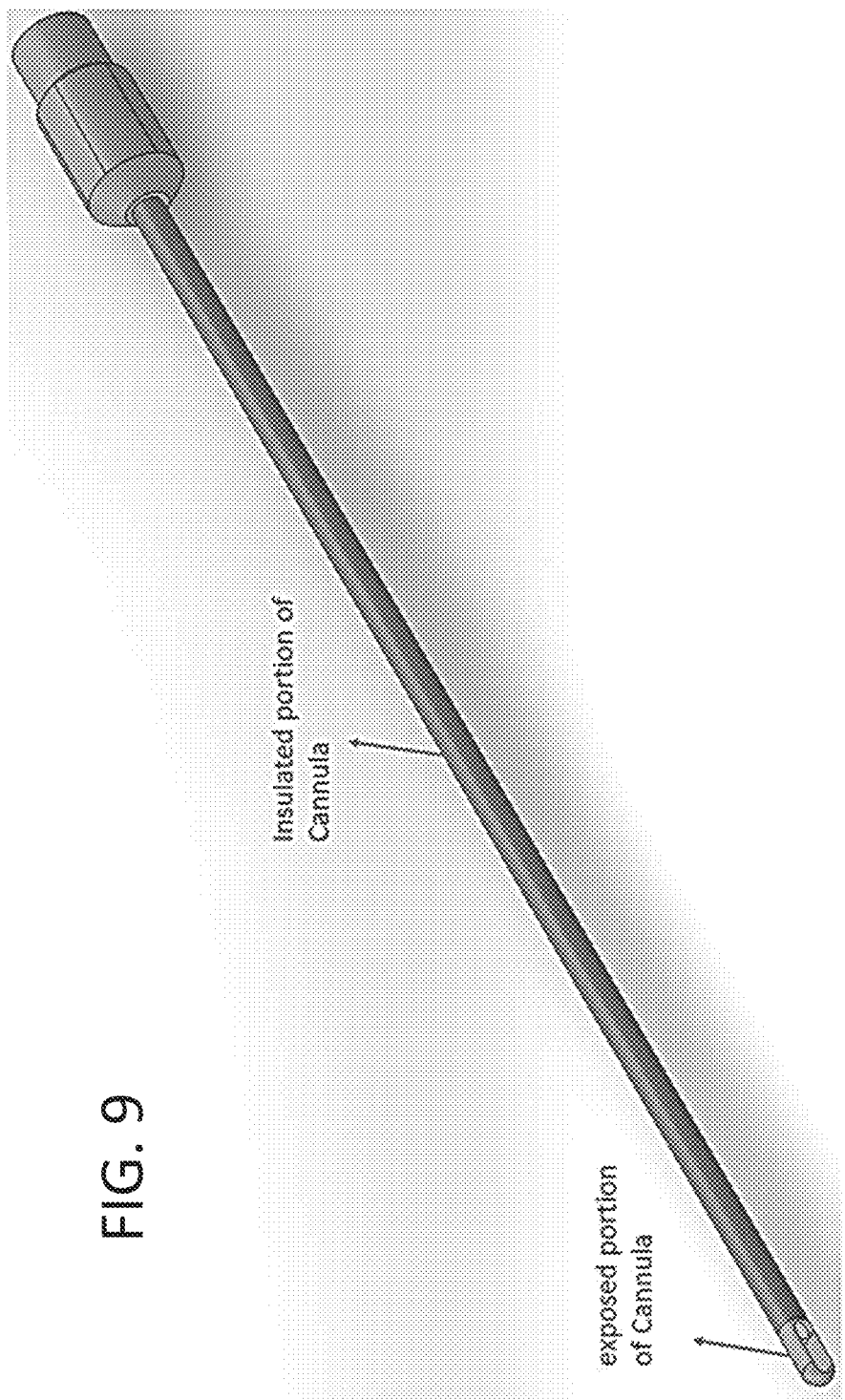
FIG. 9 shows a modified cannula where the outer body is coated with an insulating material except at the tip, allowing it to act as the first electrode.
Figure 10:
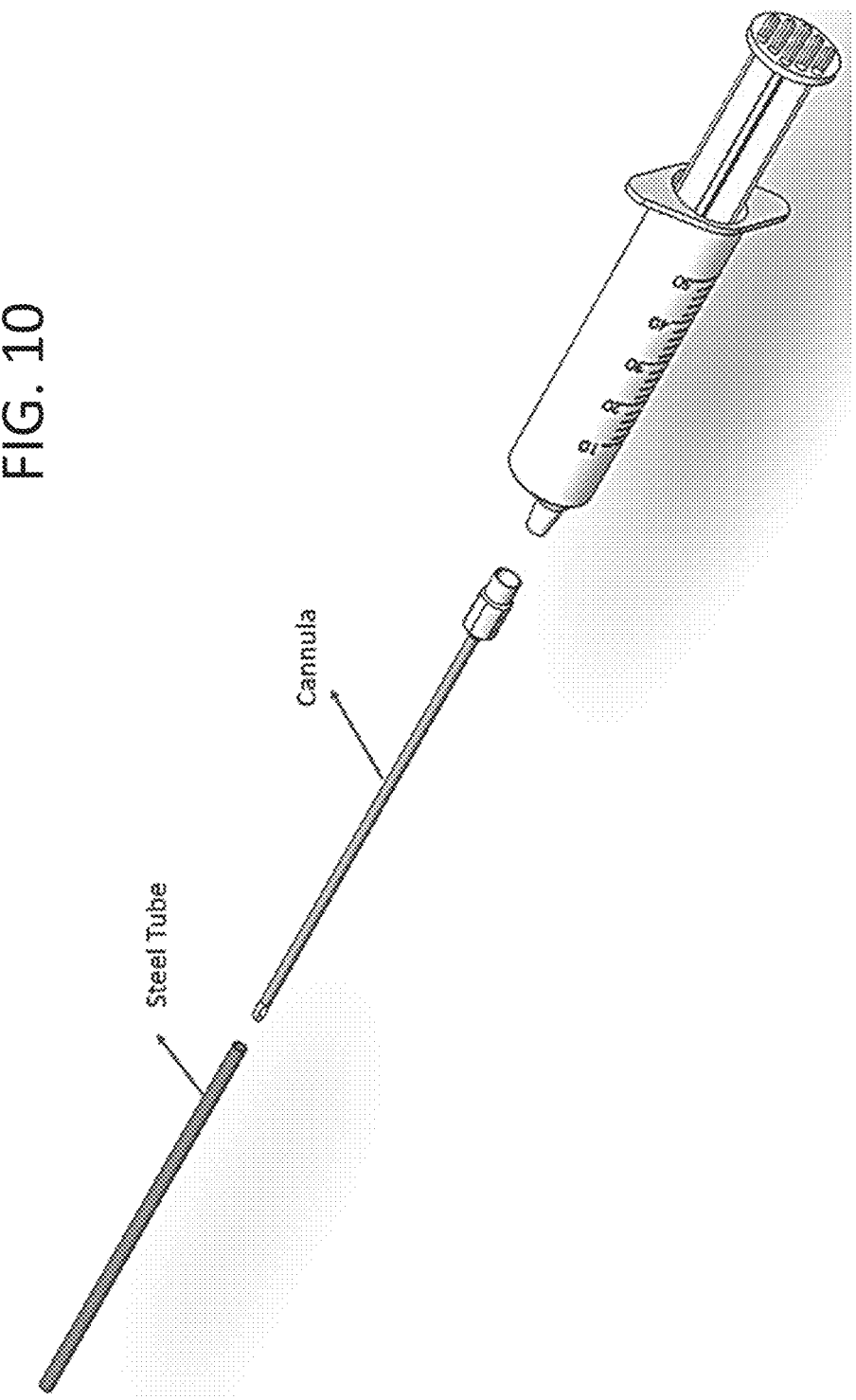
FIG. 10 is an exploded view of the modified cannula assembly.

In exemplary embodiments, a cannula (FIG. 9) acts as the first electrode, while a steel tube fitted over the cannula act as the second electrode (FIG. 10). The outer body of the cannula is covered with an insulating material (i.e. heat shrink, or polyurethane) while the tip is left exposed. Insulating the outer body of the cannula will prevent a short-circuit from occurring between the two electrodes.

Figure 11:
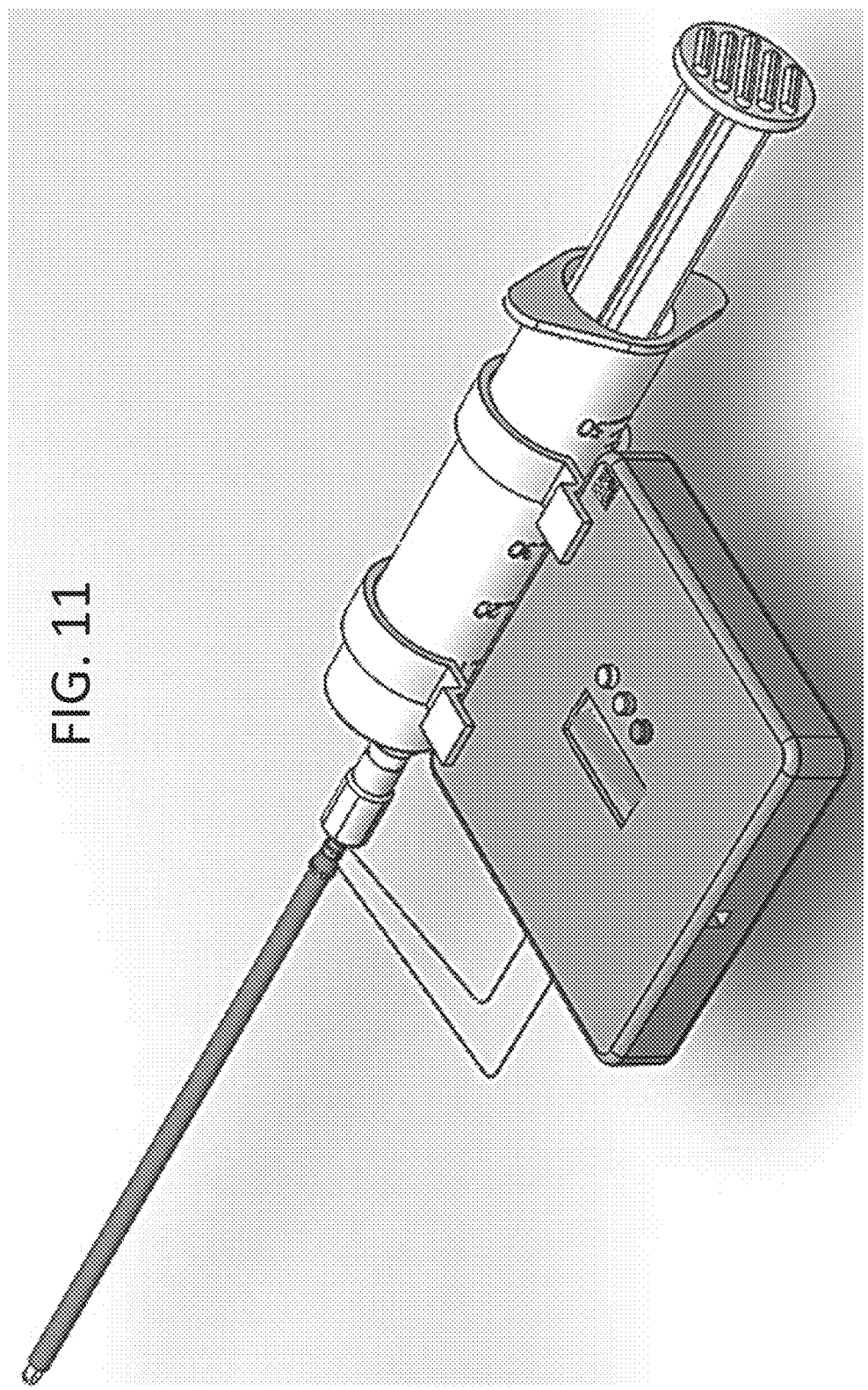
FIG. 11 is a schematic view of the cannula system including wires from the two electrodes connecting to the detector unit.

In some embodiments, the tip of the cannula serves as one of the electrodes. Although this is not mandatory and it may be desirable to have electrodes electrically separate from the cannula itself. The electrodes are connected to wires at the base of the cannula and then to an impedance sensing system (the detector unit in FIG. 11), which has been previously described. An audible alert or visual indicator (e.g. red light or blinking strobe) can be enabled to notify the surgeon when certain impedance thresholds are reached and can simultaneously trigger a valve or other mechanism to stop the flow of fat.

Figure 12:
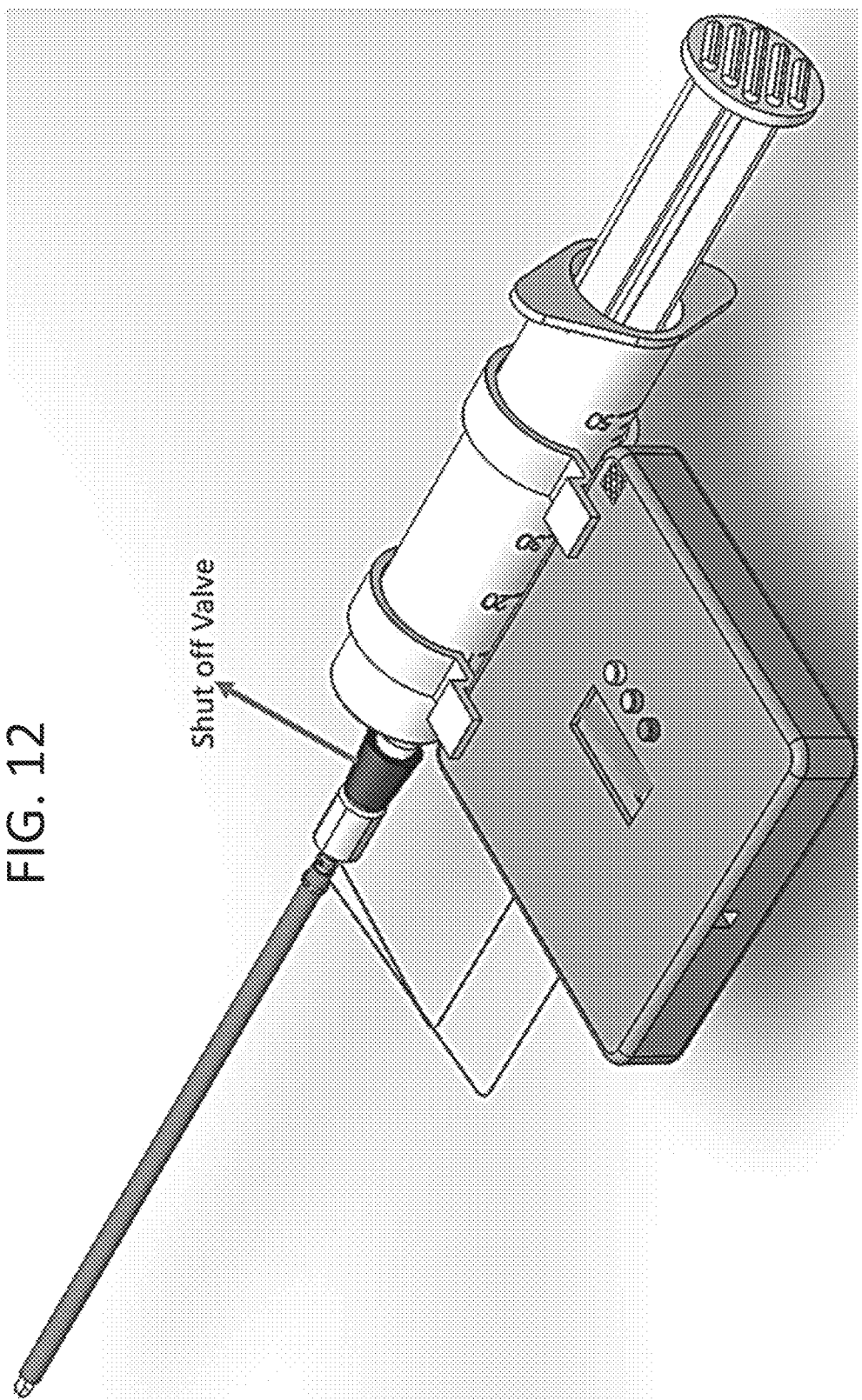
FIG. 12 is a schematic of an exemplary cannular system including a shutoff valve.
Figure 13:
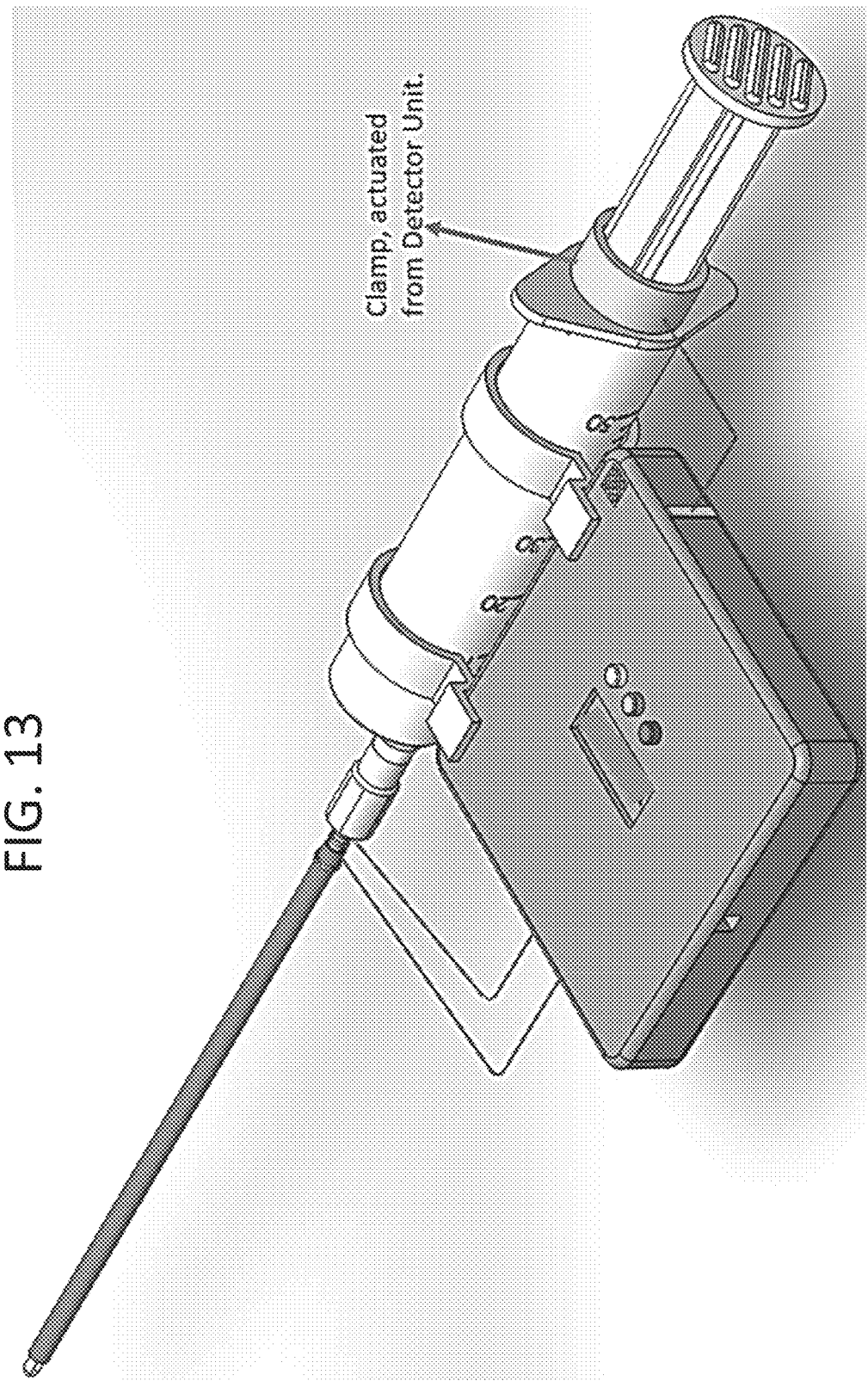
FIG. 13 is a schematic of an exemplary cannular system including a clamp for a syringe plunger.

FIGS. 12 and 13 show examples of a cannula system with electrodes and a detector unit, along with two features to stop the flow of material through the cannula. In FIG. 12, at the interface of the cannula and the syringe (although it can be placed at any location along the flow path) is a shut off valve. This valve may be any type of electromagnetic or other actuated valve that may be controlled by a microcontroller. The valve functions to stop the flow of materials (e.g. fat) through the cannula when problematic tissue (e.g. muscle or blood) is encountered by the cannula and detected by the detector unit. An algorithm executing on the microcontroller in the unit or within a logic circuit may be configured to cause the valve to automatically shut off flow when the problematics tissue is encountered, thereby relieving the user of manually stopping or disrupting the process of suction or injection.

FIG. 13 illustrates an alternative means of stopping flow through the cannula. A clamp is shown on the syringe plunger. Similar to the valve operation, if the detector unit detects that the cannula encounters problematic tissue, the clamp can impede the motion of the plunger, thereby stopping flow of material through the cannula. Just as with the valve, this device can be automatically activated, thereby relieving the user of manually stopping or disrupting the process of suction or injection. There are many possible designs of actuation devices that may clamp or otherwise brake or arrest the plunger to accomplish the same effect, and such actuation devices may be applied to cannula systems that have alternative injection or suction methods from the syringe and plunger shown here. Likewise, the valve concept and the actuator clamp can be incorporated individually or in conjunction.

In addition to the devices shown in FIGS. 12 and 13, the cannula systems described herein may incorporate a fully controlled injection or suction system, whereby the material flow is controlled by a microcontroller or other control system instead of manual control. For example, an actuator (such as a rotary or linear motor), controlled by a microcontroller, may be used to move the plunger in the syringe as shown in the figures. Such a system can have a preset rate of flow and can be automatically stopped upon detection that the cannula is encountering problematic tissue.

Exemplary Sensing Cannula Sleeves

The present disclosure describes novel methods for incorporating sensing electrodes into a cannula system. Some embodiments involve a retrofit sleeve that can be added to an existing cannula such that the sleeve fully incorporates the electrodes or couples electrically with the cannula to complete an electrode pair. Such a design is simpler than previous designs in that the components needed for enabling a sensing cannula system can be retrofitted to existing cannulas, thereby avoiding fully redesign and manufacture of the cannula. Additional features described here are alternative methods for stopping or redirecting the flow of fat or other injected materials. In other embodiments, an existing cannula can be retrofitted with a sheath which uses cannula itself as one electrode, as well as there being one or more electrodes on the sheath.

FIG. 1 shows a schematic of a cannula system comprising a detection unit, a cannula that is coupled with a syringe for injection or suction of fat and that is instrumented with electrodes for detection of tissue type, and wires providing the electrical connection to the detection unit. An additional feature of the system is an actuation system that can automatically stop the flow of fat. Several design combinations have been presented in the previous application for the system.

The disclosed technology can measure the resistance of materials that the cannula contacts as it is inserted. The resistance values can be used to indicate progress of the cannula through tissue, and can indicate when, for example, muscle has been contacted. This information can be used through various algorithms and hardware to alert the user, and/or automatically stop the flow of suctioned or injected material.

Tissue or fluid resistance constitutes a resistor that can be measured by different techniques. Some embodiments of the detection circuit (described below) can include an oscillator whose frequency of oscillation depends on the quantities of connected resistor and capacitor components. In the present embodiment, the tissue or fluid resistance between the two electrodes of the sleeve (one of which can be the cannula body itself through electrical contact with the sleeve) make up a key resistor component in the circuit. Different resistances (e.g. fatty tissue under the skin vs. blood or muscle tissue) cause the frequency of oscillation to change. By measuring this frequency, the type of tissue in contact with the cannula, and thus the location of the cannula can be determined.

Figure 14A:
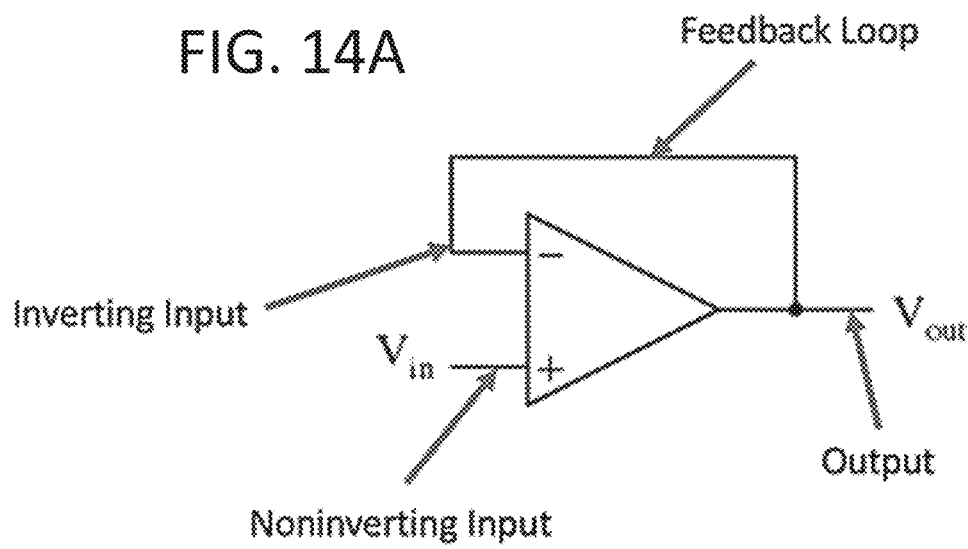
FIG. 14A is a circuit diagram of an operational amplifier (op-amp).
Figure 14B:
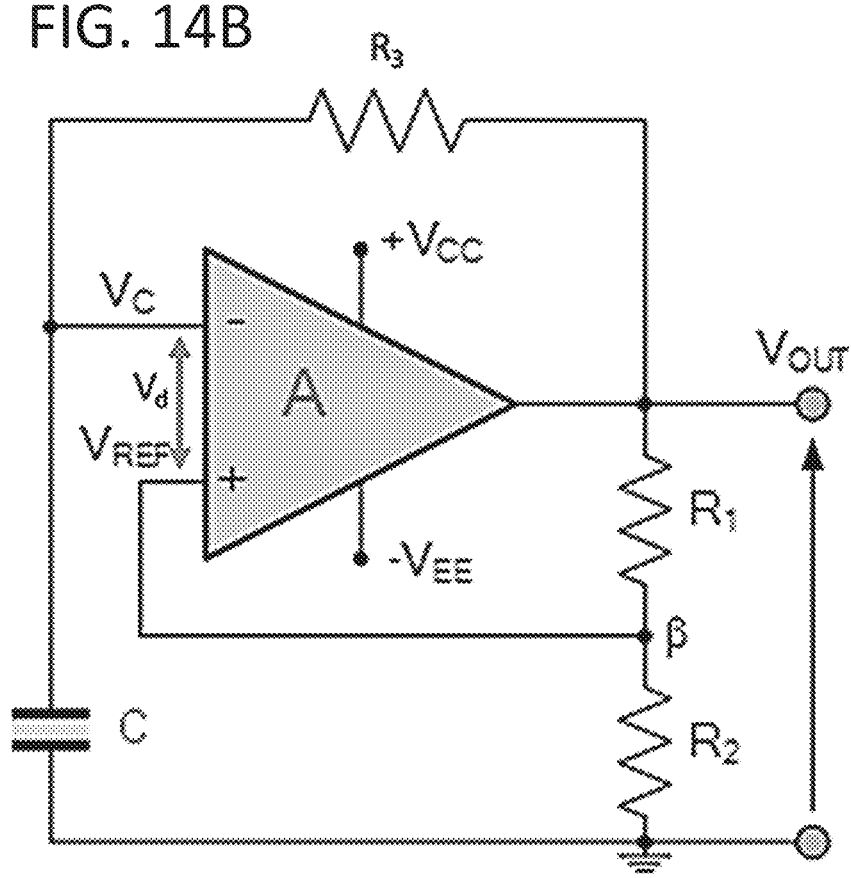
FIG. 14B is a circuit diagram of an op-amp as a multivibrator oscillator.
Figure 14C:
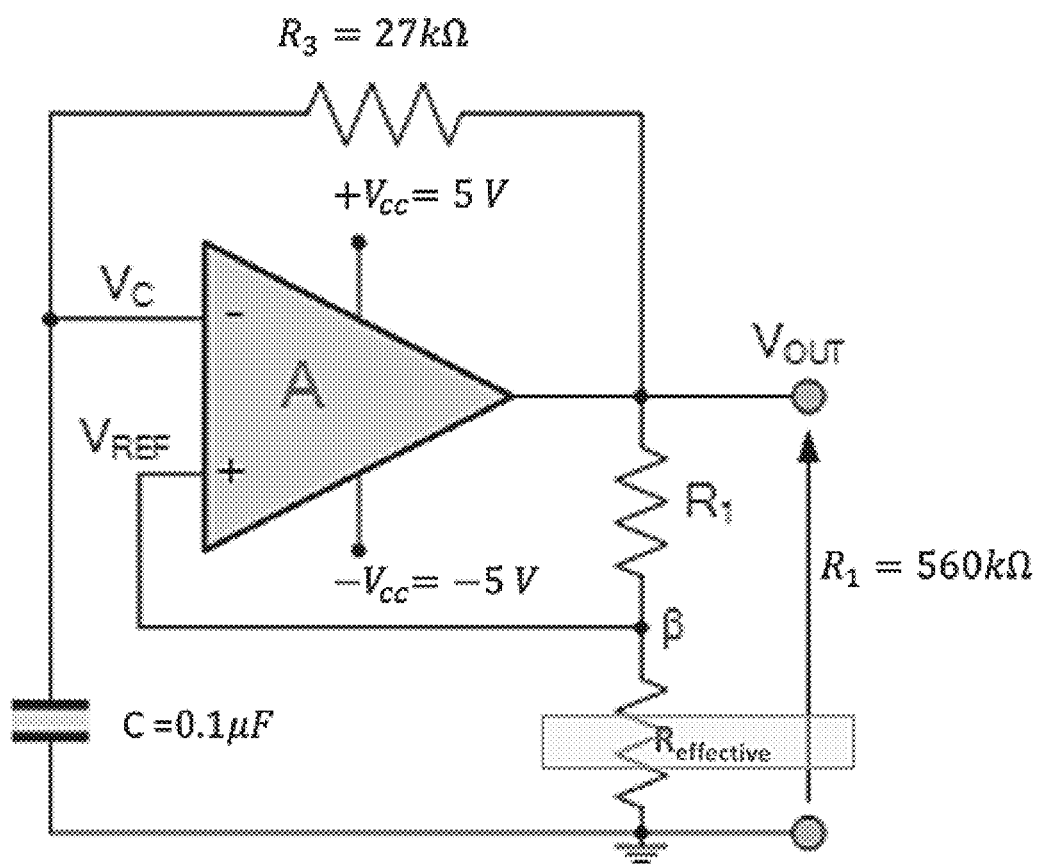
FIG. 14C is a circuit diagram of an op-amp as an astable oscillator where resistor $R_2$ is replaced with the tissue between two wire electrodes becoming the effective resistance.

FIGS. 14A-14C illustrate an example of a circuit diagram for the detection unit (100), although other types of timing circuits may be used. The circuit includes an operational amplifier (op-amp), which is an integrated circuit that can be combined with external discrete components to create a wide variety of signal processing circuits. The op-amp can comprise an active electrical component that can have connection to an external power device.

FIG. 14A displays a basic electrical schematic of an operational amplifier, including an inverting and noninverting input, an output, a feedback loop to stabilize the output. For the exemplary application disclosed here, the op-amp is operated as an astable oscillator. The operation of the op-amp is described below to clarify how it is used to measure tissue/fluid resistance in the catheter insertion systems.

FIG. 14B displays the schematic of an op-amp as an oscillator. The op-amp multivibrator is an astable oscillator circuit that generates a rectangular output waveform that switches between supply voltages $+V_{CC}$ to $-V_{EE}$, using an RC timing network.

The period of the waveform is determined by the charge/discharge rate of the capacitor, which depends on the circuit components. For the purpose of this application, the resistor $R_2$ in FIG. 14C is the effective resistance of the material (e.g., air or tissue) between the electrodes of the catheter insertion system, so the frequency of the oscillator, which is measured, is dependent on the tissue resistance.

The other circuit components may be chosen to affect the circuit behavior, such as to limit the current in the tissue being tested. For example, choosing a high resistor value for $R_1$ (e.g. 500 KΩ) ensures that the total amount of current introduced into the patient's body is below 10 µA. Any of the circuit components or other technology discussed elsewhere herein can also be implemented the disclosed sensing cannula sleeve systems.

Figure 15:
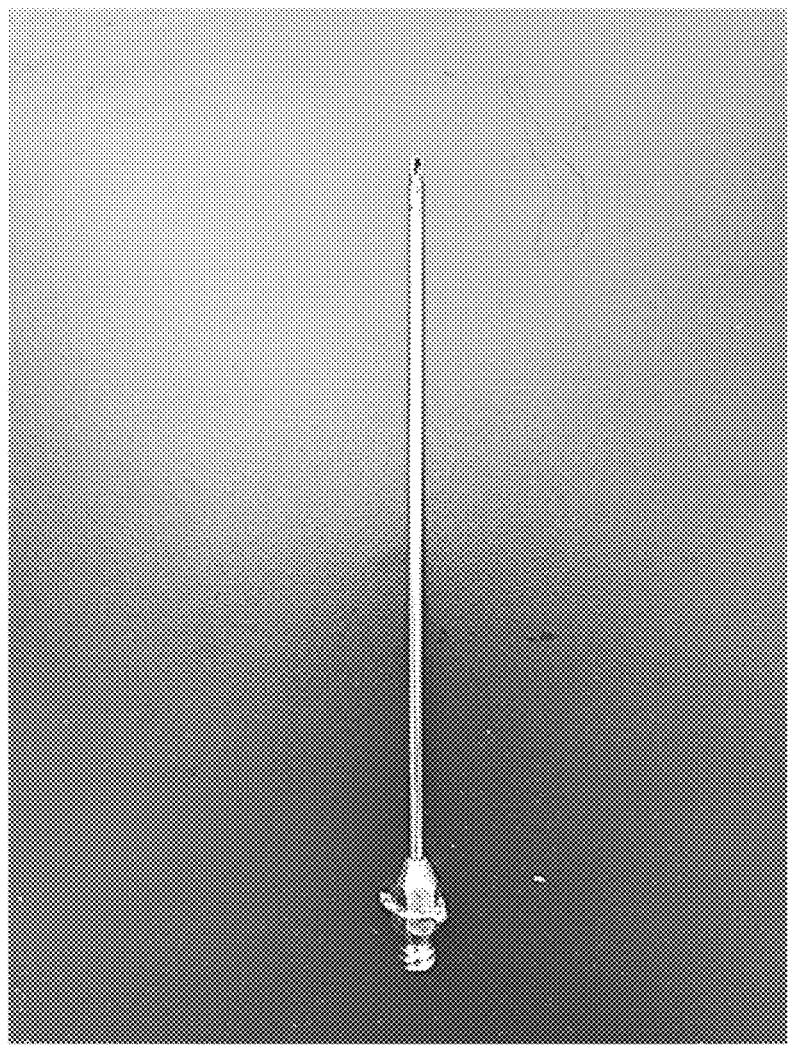
FIG. 15 shows an exemplary cannula.
Figure 16:
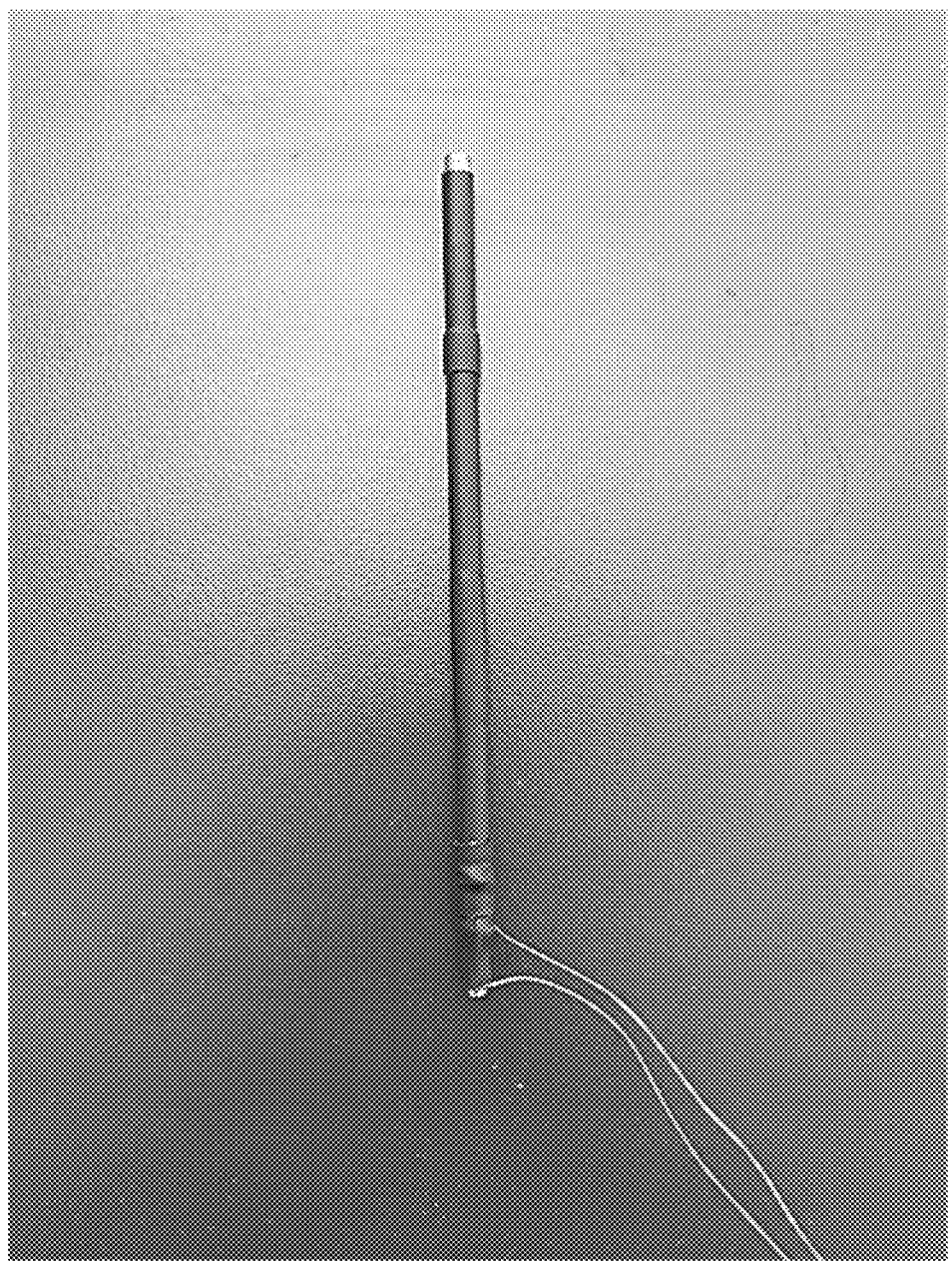
FIG. 16 shows a sensing sleeve with wires extending from the two electrodes (or in the case shown, from one electrode and from the electrical contact to the existing cannula).
Figure 17:
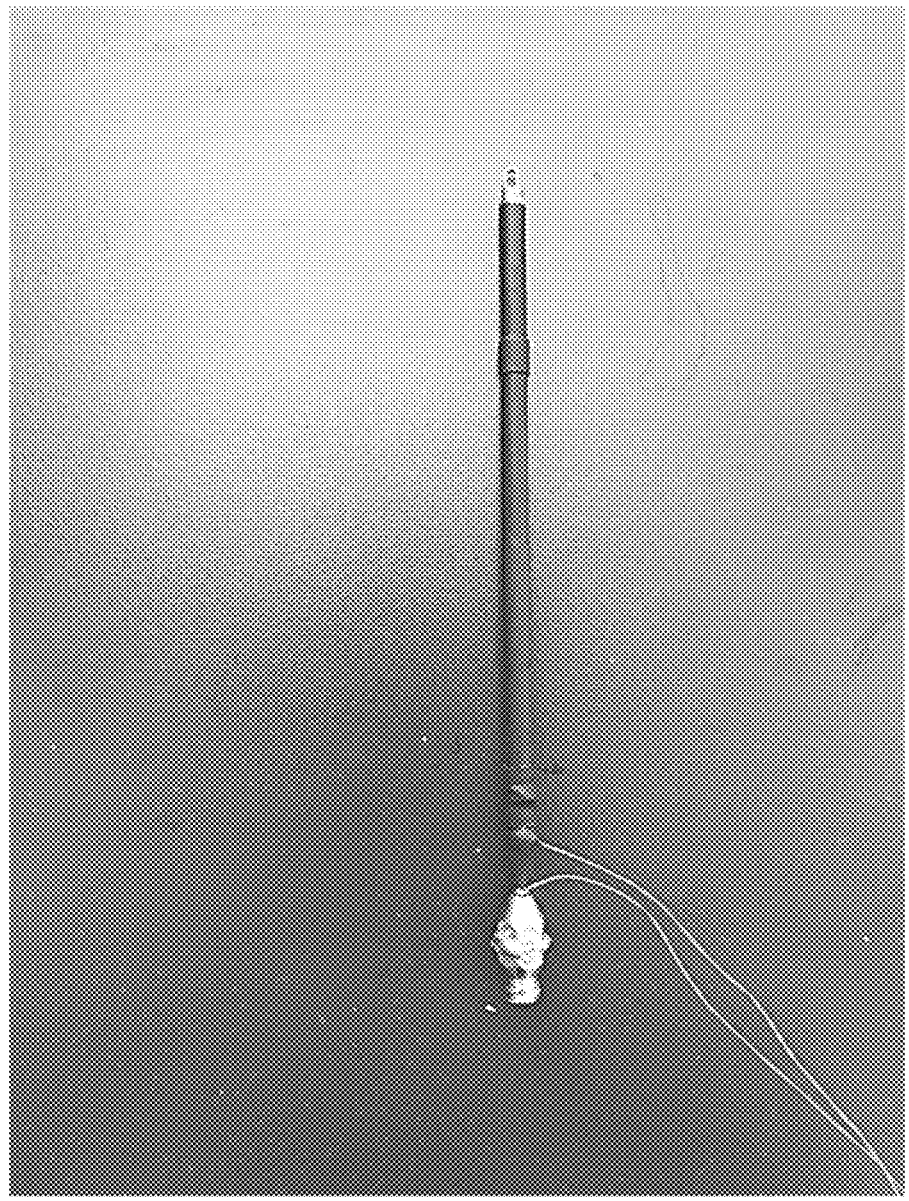
FIG. 17 shows a cannula of FIG. 15 with the sensing sleeve of FIG. 16 installed.

An example of the present sensing device, shown below, incorporates an electrode and contact into a sleeve that may be retrofitted onto an existing cannula. FIG. 15 shows an exemplary cannula. FIG. 16 shows a sleeve that is placed over the cannula to enable sensing of the tissue in which the tip of the cannula is embedded. The design shown incorporates a metal inner sleeve that makes electrical and physical contact with the cannula, thereby allowing the cannula to be one electrode. A second electrode is located near the exposed cannula tip, but electrically insulated from the first, providing an electrode pair for sensing. FIG. 17 shows the sensing sleeve assembled over the cannula. The sleeve is shaped (slightly elliptical) so that a force fit exists between the cannula and sleeve such that the sleeve and cannula may be assembled and disassembled without tools, but the friction force is high enough to prevent the sleeve from becoming dislodged during normal use. The sleeve may be secured to the cannula using other means, enabling it to be placed and removed more easily. For example, a mating end fixture may be used to couple it to the end of the cannula that receives material from a syringe or pump, or to another mating device coupled to the cannula.

Figure 18A:
FIG. 18A-18I shows fabrication/assembly steps for an exemplary sensing cannula system.
Figure 18B:
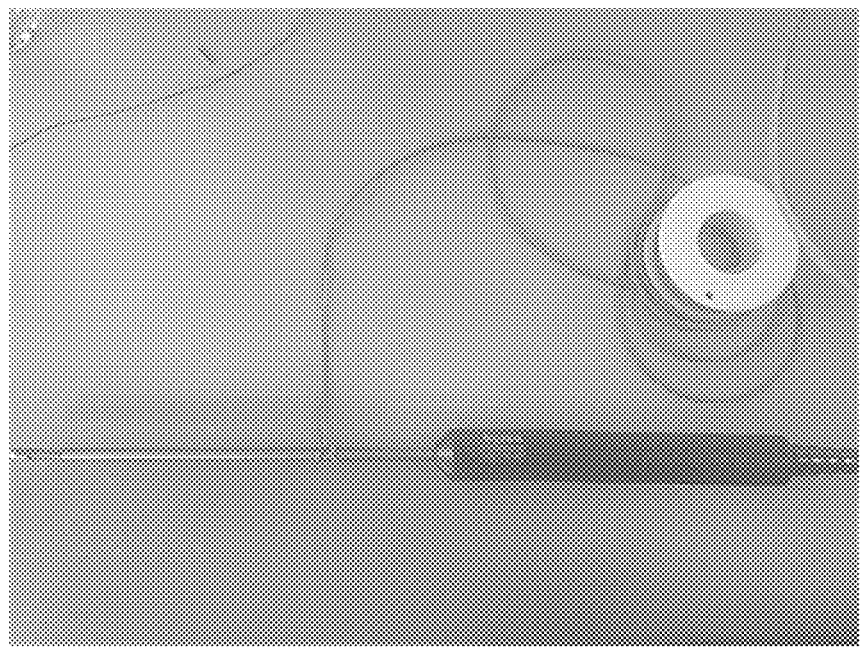
Figure 18C:
Figure 18D:
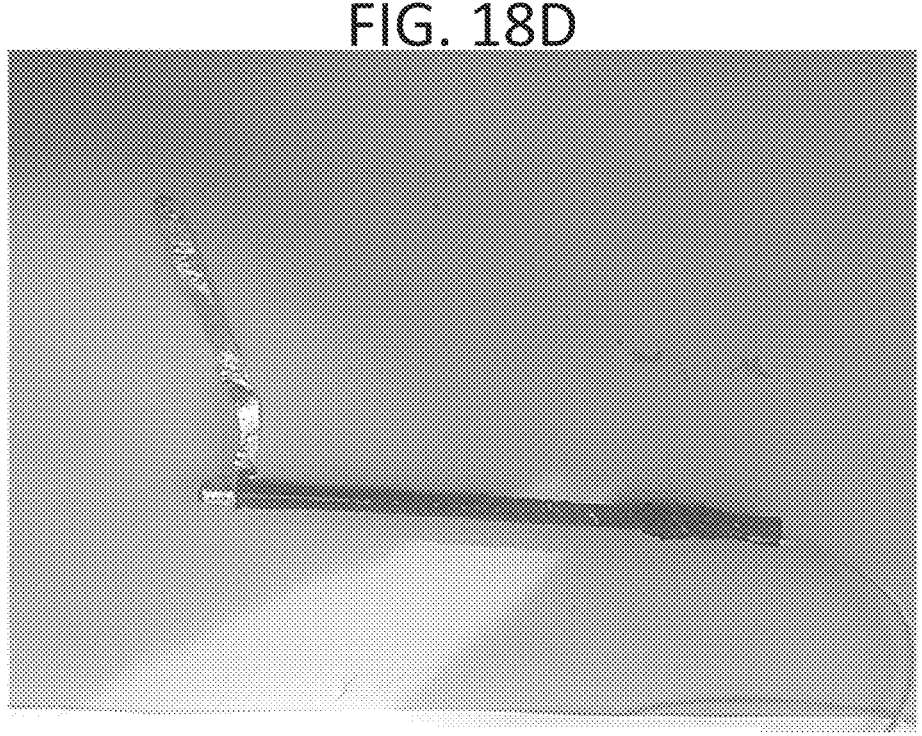
Figure 18E:
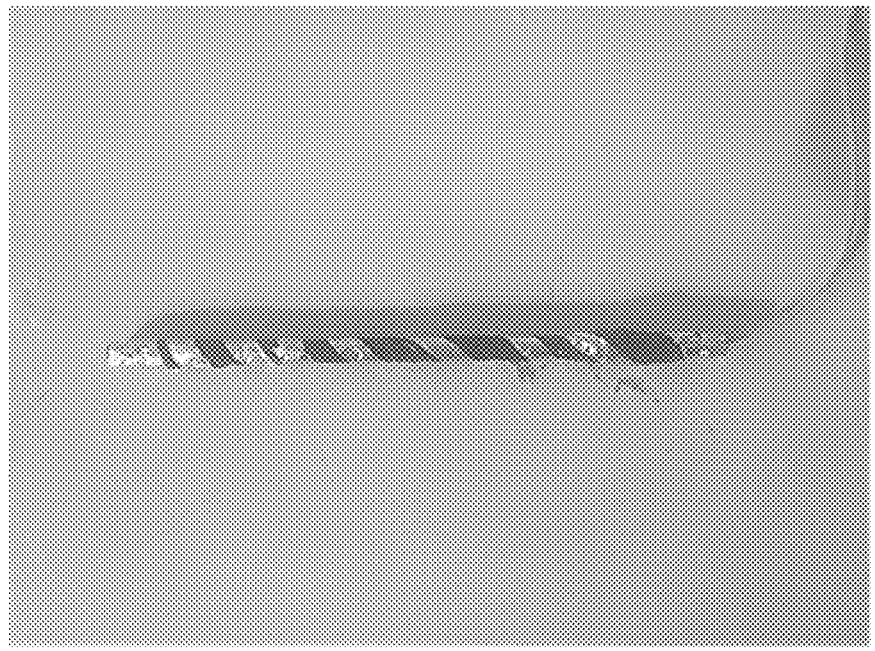
Figure 18F:
Figure 18G:
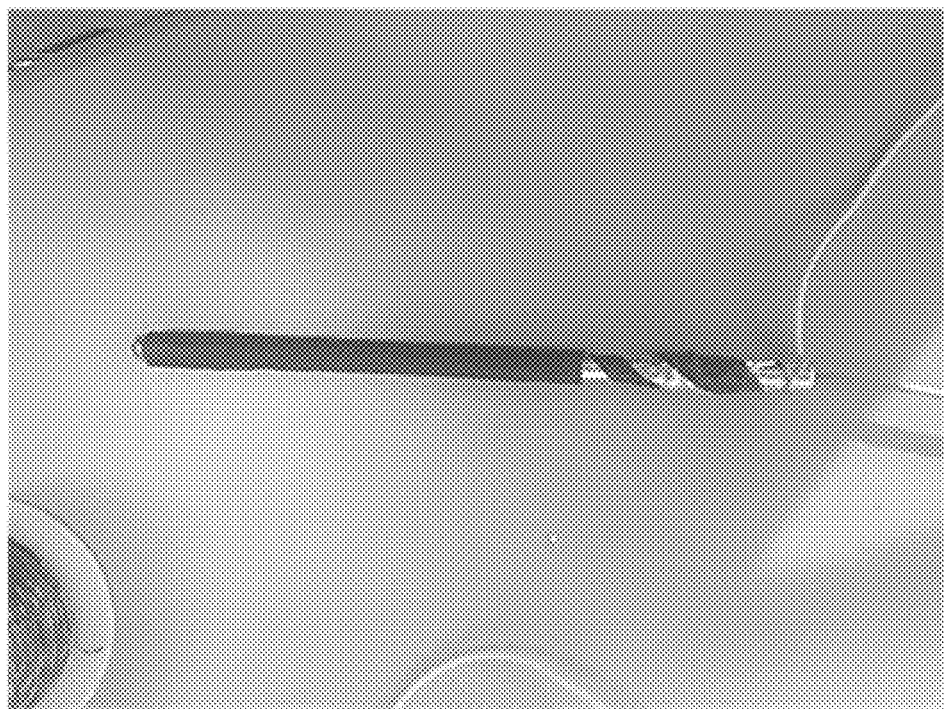
Figure 18H:
Figure 18I:
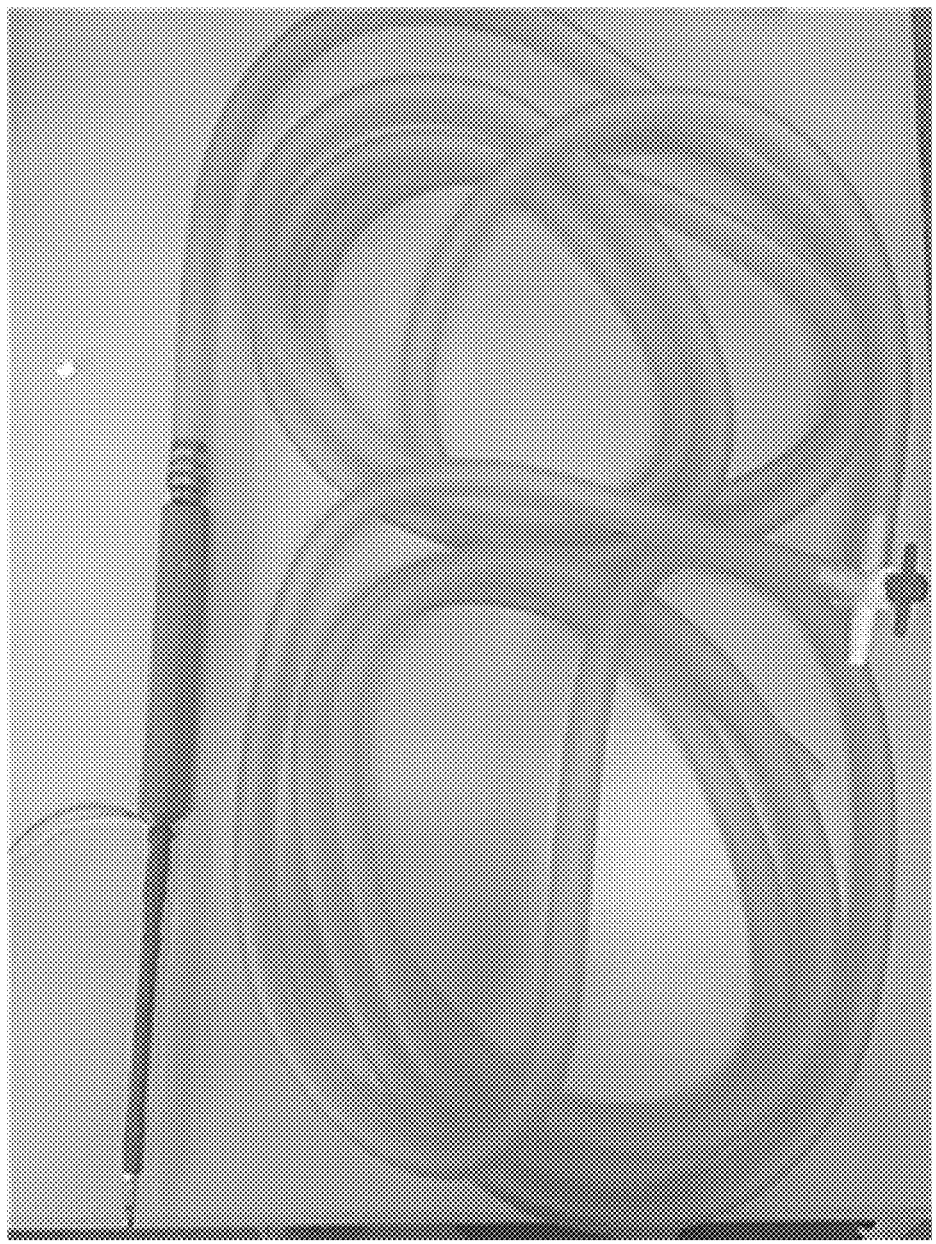

FIGS. 18A-18I show a step by step assembly process of the present sleeve, indicating the various components. FIG. 18A shows the cannula to which it is fitted. Next to the cannula is the inner metal tube that is formed to press fit onto the cannula after assembly. FIG. 18B shows a wire being attached to the inner metal tube so that the cannula, by way of the inner metal tube, can serve as one electrode in the system. FIG. 18C shows an insulating layer applied to the inner metal tube and wire, isolating it from the second electrode. The current insulator is a heat shrink polymer, although many well-known insulating materials be used. FIG. 18D shows copper tape applied around the insulating layer to serve as the second electrode. There are many ways to create the second electrode, including a wire, conductive paint, or many other known ways to apply a conductor to an insulating layer. FIG. 18E shows the second electrode wrapped along the length of the insulator so that it can be connected to a second wire toward the base of the sheath. FIG. 18F shows a partial second insulating layer covering the second electrode. FIG. 18G shows a second wire attached to the second electrode. FIG. 18H shows the sensing sleeve fully insulated with the second insulator. FIG. 18I shows the sensing sleeve assembled onto the cannula, and supply tubing connected to the cannula.

In alternative embodiments, the cannula is not used as one of the electrodes. For example, the structure can be similar to that shown in FIG. 16, however instead of one exposed second electrode at the tip, two separately wired electrodes can be used. For example, two semicircular electrodes located on either side of the tip can be used, although there are many possible arrangements of two electrodes that can be employed. The two electrodes can both be electrically insulated from the cannula, and each can have a separate wire for connection to the detection unit.

In addition to the detection functions, the cannula systems described herein can incorporate a fully controlled injection or suction system, whereby the material flow is controlled by a microcontroller or other control system instead of manual control. For example, an actuator (such as a rotary or linear motor), controlled by a microcontroller, may be used to move a plunger or otherwise actuate or pump material (e.g. fat) into the cannula. Such an actuator (plunger, motor, pump, or other material transport device) can be automatically stopped or the flow of material can be redirected automatically upon detection that the cannula is encountering problematic tissue.

Figure 19:
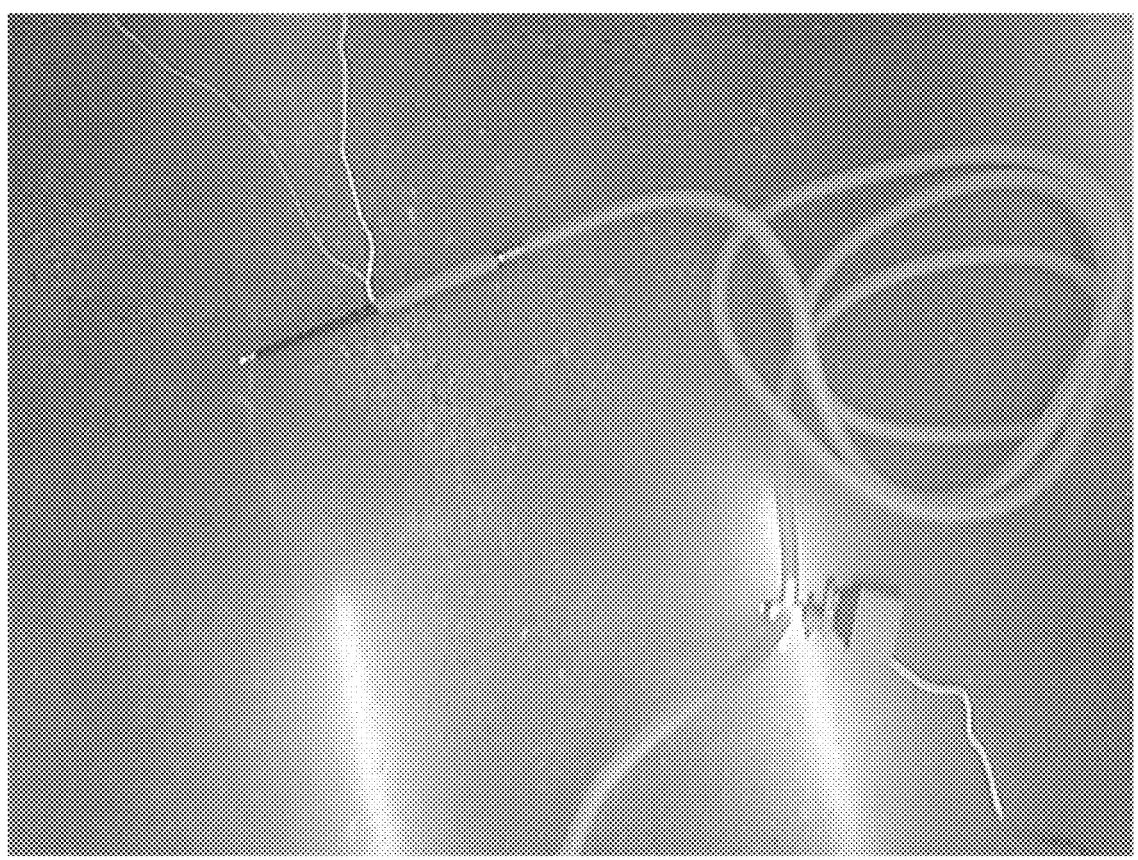
FIG. 19 shows an assembled sensing cannula system connected to a supply tube equipped with a flow control valve.

Alternatively, the flow of material may be stopped or redirected with a value. For example, FIG. 19 shows a cannula with the sensing sleeve installed. The cannula is connected to a material supply tube. The tube has installed a flow control valve. During operation, when the sensing sleeve (by way of the detection unit) detects problematic material (e.g. muscle or blood), then the microcontroller may send a signal to the control valve to shut off (or redirect) the flow of material to the cannula. In that way, the user does not need to take action, and the flow of material may be stopped so that fat is not injected into problematic areas of the body. The system may also include methods to shut off the flow of material by stopping the actuator driving the material (e.g. stop a pump supplying the fat).

In some embodiments, a sensing cannula system can comprise an array of electrodes on the distal portion of sheath and/or the cannula. Such an array of electrodes can be circumferentially arranged around the perimeter of the sheath or cannula, and/or can be arranged linearly along the sheath or cannula (e.g., multiple locations down length of cannula) to improve resolution or directionality the sensing.

While the complications related to fat grafting procedures have been most prominently investigated, liposuction is not without complications. Visceral and vascular injuries can occur during liposuction when the surgeon loses track of the location of the cannula tip and it passes into an undesired space (abdomen, chest, etc.). The sensing cannula systems disclosed herein can also be used during liposuction procedures, and can help ensure the cannula tip remains within the subcutaneous space during liposuction procedures. The sensing cannula systems used during such liposuction procedures can be similar in construction to those used in fat grafting procedures and other applications disclosed herein. In liposuction procedures, fat flow out of the body through the cannula, rather than being injected into the body. Accordingly, suction systems can used with the sensing cannula systems in such procedures, and in some embodiments the systems can automatically shut of suction, close a valve, and/or alert the operator if the system senses the cannula tip has entered an undesirable tissue location (e.g., not fat).

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically or chemically coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of the following claims.

The invention claimed is:

1. A device comprising a metal cannula with two electrodes at or near a tip of the cannula operable to measure impedance of tissue adjacent to the tip of the cannula, wherein the cannula is operable as a first electrode of the two electrodes and a removable sheath positionable over the cannula comprises a second electrode of the two electrodes, the removable sheath further comprising an electrical insulation layer between the cannula and the second electrode that electrically insulates the cannula from the second electrode, wherein an impedance sensing system is electrically coupled to the cannula and electrically coupled to the second electrode to measure impedance of tissue adjacent the tip of the cannula, and wherein the removable sheath comprises a conductor that makes electrical contact with the cannula when the removable sheath is positioned over the cannula.

2. The device of claim 1, wherein the tip of the cannula is exposed and serves as the first electrode.

3. The device of claim 1, further comprising an audible or visual indicator that notifies a user when a predetermined impedance threshold value is detected.

4. The device of claim 1, further comprising a valve or clamp configured to close the cannula to stop flow of fat or other material through the cannula based on a measured impedance value.

5. A method comprising measuring impedance of biological material adjacent to the cannula of the device of claim 1, and determining an identity of the material based on the measured impedance.

6. The method of claim 5, further comprising closing or opening the cannula based on the determined identity of the material adjacent to the cannula.

7. The method of claim 5, further comprising preventing material from flowing through the cannula based on the determined identity of the material adjacent to the cannula.

8. The method of claim 7, further comprising closing a valve or stopping a pump to prevent material from flowing through the cannula.

9. A system comprising:
a cannula having a distal tip and operable as a first electrode;
a removable sheath positioned over the cannula, the sheath comprising a second electrode positioned adjacent a distal end of the sheath and an electrical insulation layer between the cannula and the second electrode, wherein the electrical insulation layer electrically insulates the cannula from the second electrode; and
an impedance sensing system electrically coupled to the cannula and also electrically coupled to the second electrode;
wherein the cannula, the second electrode, and the impedance sensing system are operable to measure impedance of tissue adjacent to the distal tip of the cannula.

10. The system of claim 9, wherein the sheath comprises a conductor that makes electrical contact with the cannula when the sheath is positioned over the cannula.

11. The system of claim 10, wherein the conductor is a metallic inner sleeve positionable around the cannula in electrical contact with the cannula.

12. The system of claim 9, wherein the sheath comprises:
a first electrical conductor that is in electrical contact with the cannula when the sheath is positioned over the cannula and is electrically coupled to the impedance sensing system; and
a second electrical conductor that extends from the second electrode proximally along an axial length of the sheath and is electrically coupled to the impedance sensing system while being electrically insulated from the cannula and the first electrical conductor.

13. The system of claim 9, further comprising an audible or visual indicator that notifies a user when a predetermined impedance threshold is sensed.

14. The system of claim 9, further comprising a valve or clamp configured to stop flow of adipose tissue or other material through the cannula based on a measured impedance value.

15. The system of claim 14, wherein the system comprises a valve, and the valve is actuatable to shut off flow of material through the cannula based on a measured impedance value.

16. The system of claim 14, wherein the system comprises a clamp;
the system further comprises a syringe coupled to the cannula; and
the clamp is operable to impede motion of a plunger of the syringe based on a measured impedance value.

17. The system of claim 9, further comprising an array of electrodes on a distal portion of the sheath or the cannula, the array of electrodes being arranged to improve resolution or directionality of impedance sensing.

18. The system of claim 17, wherein the array of electrodes is arranged linearly along a length of the sheath or cannula and/or circumferentially around the sheath or cannula.

19. The system of claim 9, wherein the system is operable to perform fat grafting and/or liposuction.

20. The system of claim 9, wherein the system is operable to distinguish adipose tissue from muscle tissue based on sensed impedance.

21. The system of claim 9, wherein the system is operable to stop flow of material through the cannula when the system determines that the distal tip of the cannula is adjacent muscle tissue, and operable to allow flow of material through the cannula when the system determines that the distal tip is adjacent adipose tissue.

22. A system comprising:
a cannula having a distal tip and operable as a first electrode;
a removable sheath positioned over the cannula, the sheath comprising a second electrode positioned adjacent a distal end of the sheath and an electrical insulation layer between the cannula and the second electrode, wherein the electrical insulation layer electrically insulates the cannula from the second electrode; and
an impedance sensing system electrically coupled to the cannula and also electrically coupled to the second electrode;
wherein the cannula, the second electrode, and the impedance sensing system are operable to measure impedance of tissue adjacent to the distal tip of the cannula; and
wherein the system further comprises a clamp and a syringe coupled to the cannula, and the clamp is operable to impede motion of a plunger of the syringe based on a measured impedance value to stop flow of adipose tissue or other material through the cannula.

* * * * *